(12) United States Patent
Saito et al.

(10) Patent No.: US 6,893,412 B2
(45) Date of Patent: May 17, 2005

(54) PLATELET COLLECTING APPARATUS

(75) Inventors: Noboru Saito, Kanagawa (JP); Takeshi Udagawa, Kanagawa (JP); Kunio Horiuchi, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 468 days.

(21) Appl. No.: 09/994,696

(22) Filed: Nov. 28, 2001

(65) Prior Publication Data

US 2002/0099319 A1 Jul. 25, 2002

(30) Foreign Application Priority Data

Nov. 28, 2000 (JP) .......................... 2000-360786

(51) Int. Cl.$^7$ .......................... A61M 37/00; B01D 33/15; C02F 1/38
(52) U.S. Cl. .................... 604/6.01; 604/6.02; 604/4.01; 604/6.04; 210/782
(58) Field of Search ...................... 604/6.04, 4.01–4.04, 604/5.01, 6.05–6.06, 6.01, 6.11, 6.15; 210/781–782, 739

(56) References Cited

U.S. PATENT DOCUMENTS

| | | | |
|---|---|---|---|
| 4,968,295 A | 11/1990 | Neumann | |
| 5,494,592 A | 2/1996 | Latham, Jr. et al. | |
| 5,607,579 A | 3/1997 | Latham, Jr. et al. | |
| 5,833,866 A * | 11/1998 | Brown | 210/739 |
| 6,334,842 B1 * | 1/2002 | Hlavinka et al. | 494/36 |
| 6,497,674 B1 * | 12/2002 | Steele et al. | 604/6.01 |
| 6,678,040 B1 * | 1/2004 | Suzuki | 356/39 |

FOREIGN PATENT DOCUMENTS

| | | |
|---|---|---|
| EP | 0 976 414 A2 | 2/2000 |
| EP | 0 992 256 A2 | 4/2000 |
| JP | 2000-84066 A | 3/2000 |
| WO | 94/25086 A1 | 11/1994 |
| WO | WO 99/11305 A1 | 3/1999 |

* cited by examiner

*Primary Examiner*—Angela D. Sykes
*Assistant Examiner*—Leslie Deak
(74) *Attorney, Agent, or Firm*—Burns, Doane, Swecker & Mathis, L.L.P.

(57) ABSTRACT

A platelet collecting apparatus 1 comprises a centrifugal separator 20 possessing a rotatable rotor 142; a first line 21 for allowing the flow of the blood entering the centrifugal separator 20; a second line 22 for allowing the flow of the blood emanating from the centrifugal separator, a plasma collecting bag 25 connected to the first line 21 and the second line 22 so as to collect the plasma emanating from the centrifugal separator 20 and return the collected plasma to the centrifugal separator 20, a platelet collecting bag 26 connected to the second line 22 so as to collect the platelets emanating from the centrifugal separator 20, a blood delivering pump 11 disposed in the first line 21, and a controller 13 for controlling the operation of the rotor of the centrifugal separator 20 and the operation of the blood delivering pump 11. The controller 13 is endowed with a function of varying the rotational frequency of the rotor 142 during the course of blood collection in conformity with the amount of the blood entered into the centrifugal separator 20 via the first line 21.

15 Claims, 20 Drawing Sheets

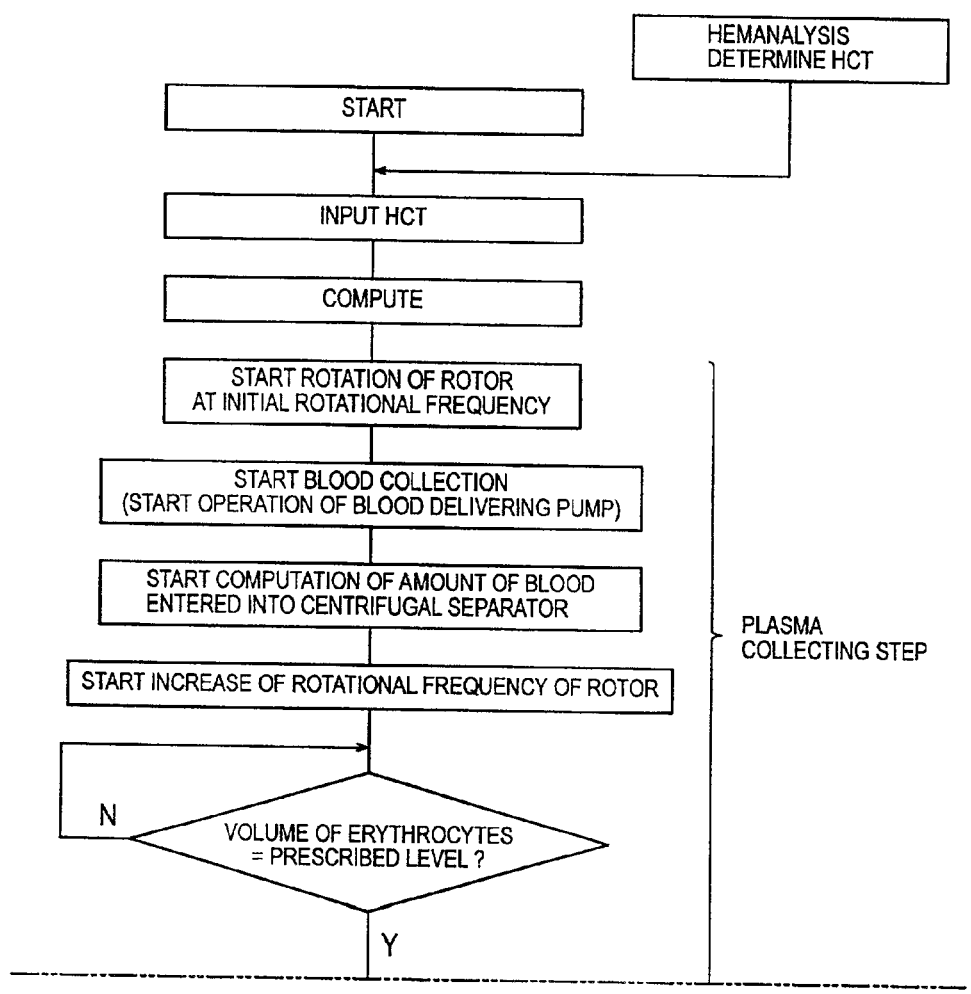

| FIG. 13A |
| FIG. 13B |

| FIG. 14A |
|----------|
| FIG. 14B |

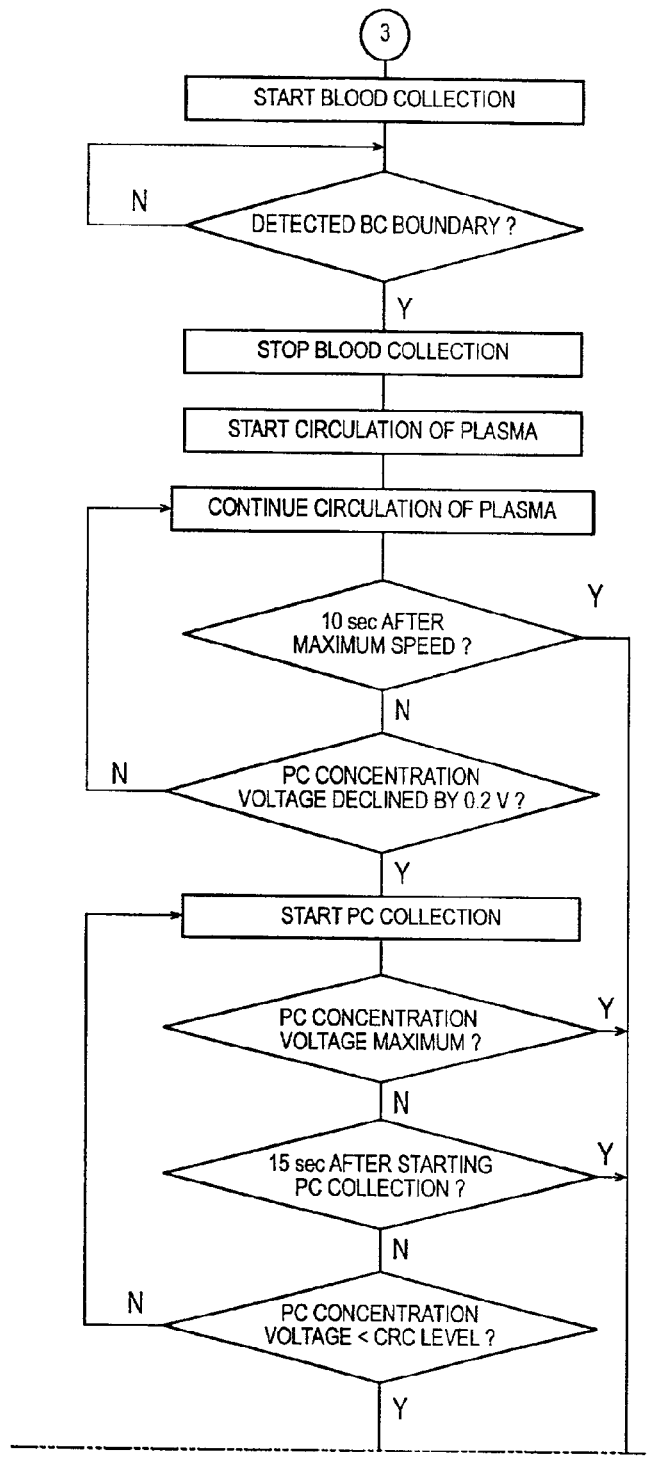

PLATELET COLLECTING APPARATUS

BACKGROUND OF THE INVENTION

1. Field of the Invention

This invention relates to an apparatus for collecting platelets from blood.

2. Description of the Related Art

The blood component collection is prevailing at present in the field of blood collection by such reasons as for effectively utilizing blood and reducing the donor's burden. This blood component collection comprises separating collected blood as by means of centrifugation into the blood components, isolating such a blood component as is necessary for a prospective donee, and returning the rest of blood components to the donor. When the blood component collection is aimed at producing a pharmaceutical preparation using a specific blood component, it adopts a procedure which comprises introducing the blood collected from the donor into a platelet collecting circuit and separating it by means of a centrifugal separator called a centrifugal bowl and disposed in the platelet collecting circuit into blood plasma, leukocytes, blood platelets, and erythrocytes. Of these blood components, the platelets are recovered in a container and used as a raw material for the platelet preparations, part of the plasma is also recovered in a container and used as a raw material for the plasma preparations or plasma derivatives, and the remainder of plasma, the leukocytes, and the erythrocytes are returned to the donor.

As a conventional platelet collecting apparatus, WO94/25086 (Publication of Unexamined Japanese Patent Application No. JP-A-08-509403), for example, discloses an apparatus for exalting the purity and the yield of platelets separated from the donated whole blood in a centrifugal separator. By this apparatus, the whole blood in the centrifugal separator is diluted at a first flow rate with such a circulating liquid as plasma or physiological saline water and further mixed before entering the centrifugal separator with the whole blood which will be subsequently collected. The plasma is circulated at a second flow rate through the centrifugal separator. Consequently, the separation between the intermediate density components in the buffy coat, namely the platelets and the leukocytes, is enhanced. Then, the plasma is circulated at a third flow rate through the centrifugal separator. While the plasma is being circulated at the third flow rate, the platelets emanate from the centrifugal separator. This procedure is intended to exalt the purity and the yield of the platelets separated from the donated whole blood. This apparatus, however, is at a disadvantage in incurring an unduly high cost of production and entailing an addition to the size of equipment because it necessitates use of three pumps, i.e. a blood collecting pump, a circulating pump, and an anticoagulant pump.

EP 0992256 A2 (Publication of Unexamined Japanese Patent Application No. JP-A-2000-107279) discloses a blood component collecting apparatus which, owing to decreasing the number of pumps to two, attains reduction in size of the apparatus, allays possible contamination of leukocytes, and allows high efficiency in the collection of platelets. This blood component collecting apparatus is furnished with a blood pump, an anticoagulant pump, a centrifugal separator driving unit, a plurality of flow path switching means, and a controller for controlling the operations of the two pumps, centrifugal separator driving unit, and plurality of flow path switching means. In this apparatus, the controller controls the operations of the two pumps, centrifugal separator driving unit, and plurality of flow path switching means and the subsequent processing steps are executed sequentially. To be specific, the plasma collecting step for collecting the blood incorporating therein the anticoagulant by actuating the blood pump and the anticoagulant pump and collecting the plasma into a plasma collecting bag by actuating the centrifugal separator driving unit; the constant rate plasma circulating step for suspending the blood collection and circulating the plasma in the plasma collecting bag to the centrifugal separator; the second plasma collecting step for actuating the centrifugal separator driving unit and collecting the plasma; the accelerated plasma circulating step for suspending the blood collection and circulating at an accelerated rate the plasma in the plasma collecting bag; the platelet collecting step; and the blood returning step are executed.

Publication of Unexamined Japanese Patent Application No. JP-A-2000-84066discloses a platelet collecting apparatus which is intended to exalt the efficiency of collection of platelets despite the use of three pumps. This apparatus increases or decreases the rotational frequency of a centrifugal separator or a circulating pump in conformity with the donor's hematocrit value. This apparatus, however, maintains the rotational frequency of the centrifugal separator constantly at a fixed level between the time the blood incorporating therein the anticoagulant is collected in the centrifugal separator and the time the platelets in the centrifugal separator are collected into the platelet collecting bag. The apparatus, therefore, is at a disadvantage in compelling the blood components (particularly the erythrocytes) separated in the centrifugal separator to be excessively compressed.

SUMMARY OF THE INVENTION

This invention, produced with a view to overcoming the problems of prior art mentioned above has for an object thereof the provision of a platelet collecting apparatus which does not noticeably suffer contamination of leukocytes and enjoys high efficiency in collection of platelets.

One aspect of this invention concerns a platelet collecting apparatus which comprises a centrifugal separator possessing a rotatable rotor having a blood storing space formed therein and an inlet and an outlet both communicating with the blood storing space and centrifugally separating the blood introduced through the inlet inside the blood storing space by virtue of the rotation of the rotor; a first line for allowing the flow of the blood entering the centrifugal separator; a second line for allowing the flow of the blood emanating from the centrifugal separator; a plasma collecting bag connected to the first line and the second line so as to permit collection of the plasma emanating from the centrifugal separator and return of the collected plasma to the centrifugal separator; a platelet collecting bag connected to the second line so as to permit collection of the platelets emanating from the centrifugal separator; a blood delivering pump disposed in the first line; and a controller for controlling the operation of the rotor of the centrifugal separator and the operation of the blood delivering pump, the controller being endowed with a function of changing the rotational frequency of the rotor during the course of blood collection in conformity with the amount of the blood to flow in the centrifugal separator via the first line.

The platelet collecting device described above, owing to the effect of increasing or decreasing the rotational frequency of the rotor of the centrifugal separator during the course of blood collection, is enabled to manifest high efficiency in collection of the platelets and, at the same time, attain collection of the platelets in a state entailing no noticeable contamination of leukocytes.

Another aspect of this invention concerns a platelet collecting apparatus which comprises a centrifugal separator possessing a rotatable rotor having a blood storing space formed therein and an inlet and an outlet both communicating with the blood storing space and centrifugally separating the blood introduced through the inlet inside the blood storing space by virtue of the rotation of the rotor; a first line for allowing the flow of the blood entering the centrifugal separator; a second line for allowing the flow of the blood emanating from the centrifugal separator; a plasma collecting bag connected to the first line and the second line so as to permit collection of the plasma emanating from the centrifugal separator and return of the collected plasma to the centrifugal separator; a platelet collecting bag connected to the second line so as to permit collection of the platelets emanating from the centrifugal separator; a blood delivering pump disposed in the first line; and a controller for controlling the rotational frequency of the rotor of the centrifugal separator and the operation of the blood delivering pump, the controller being endowed with a function of circulating the plasma collected in the plasma collecting bag at an accelerating rate to the centrifugal separator and a function of changing the rotational frequency of the rotor in conformity with the speed of the circulation of the plasma being circulated by the function of effecting circulation at an accelerating rate.

The platelet collecting apparatus described above, owing to the effect of increasing simultaneously the resistance generated by the motion of the plasma and the centrifugal force during the movement of the plasma in the interstices between adjacent blood cells, is enabled to enjoy high efficiency in collection of the platelets and, at the same time, attain collection of the platelets in a state entailing no noticeable contamination of leukocytes.

The other objects, characteristics, and features of this invention will become apparent from reading the following description and referring to the preferred embodiments illustrated in the accompanying drawings.

DETAILED DESCRIPTION OF THE PREFERRED EMBODIMENTS

Figure 1:
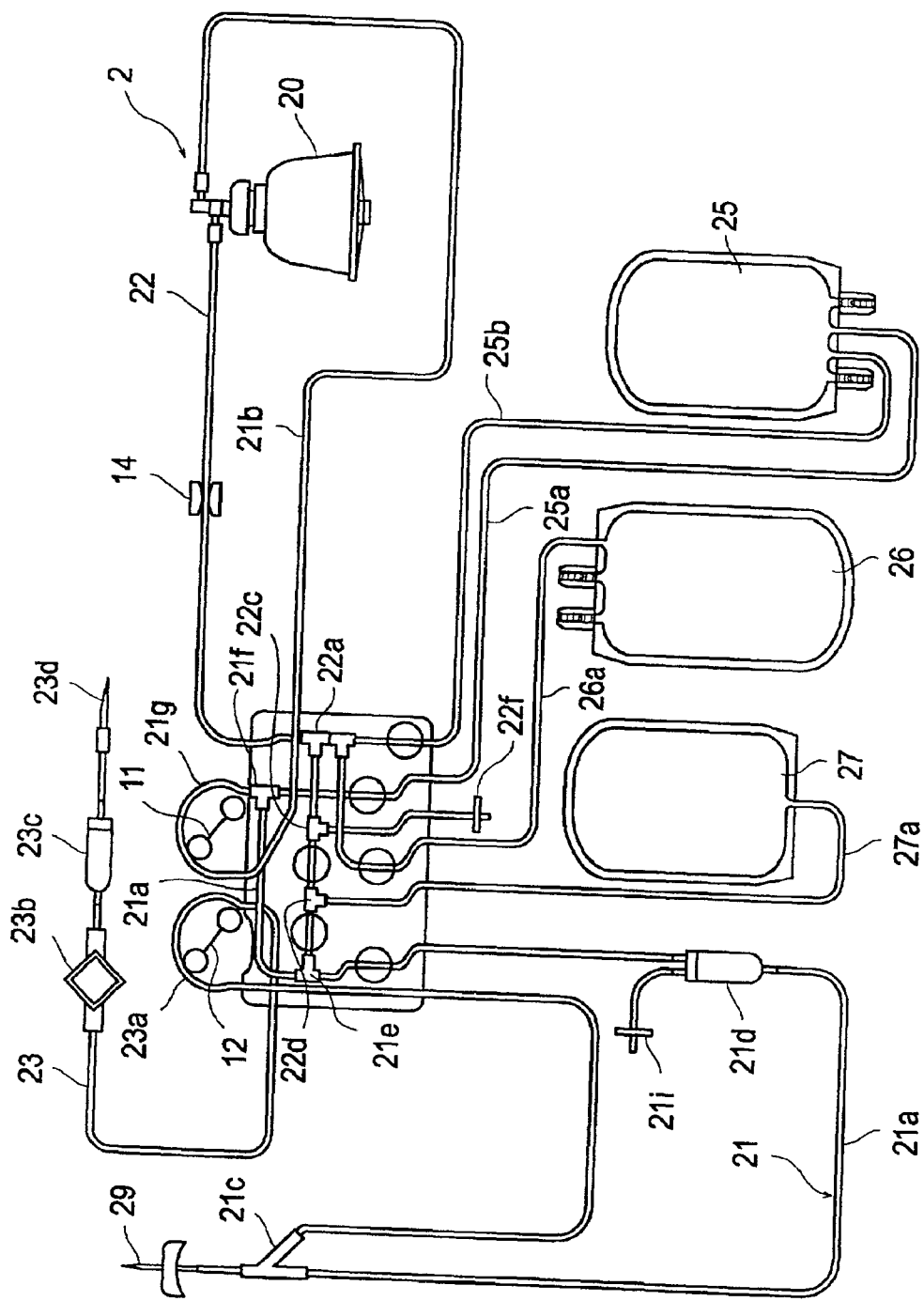
FIG. 1 is a plan view illustrating one example of the configuration of a platelet collecting circuit to be used in the platelet collecting apparatus of this invention.

The platelet collecting apparatus of this invention will be described in detail below based on the preferred embodiments illustrated in the accompanying drawings.

A platelet collecting apparatus 1 contemplated by this invention will be outlined below with reference to FIG. 1~FIG. 4. The platelet collecting apparatus 1 comprises a centrifugal separator 20 possessing a rotatable rotor 142 having a blood storing space formed therein and an inlet 143 and an outlet 144 both communicating with the blood storing space and centrifugally separating the blood introduced through the inlet 143 by virtue of the rotation of the rotor 142; a first line 21 for allowing the flow of the blood entering the centrifugal separator 20; a second line 22 for allowing the flow of the blood emanating from the centrifugal separator 20; a plasma collecting bag 25 connected to the first line 21 and the second line 22 so as to collect the plasma emanating from the centrifugal separator 20 and return the collected plasma to the centrifugal separator 20; a platelet collecting bag 26 connected to the second line 22 so as to collect the platelets emanating from the centrifugal separator 20; a blood delivering pump 11 disposed in the first line 21; and a controller 13 for controlling the operation of the rotor 142 of the centrifugal separator 20 and the operation of the blood delivering pump 11.

In the platelet collecting apparatus 1 of this invention, the controller 13 possesses the function of changing the rotational frequency of the rotor 142 in conformity with the amount of the blood introduced via the first line 21 into the centrifugal separator 20 during the course of blood collection. This function will be referred to as "the function of controlling the rotor's rotational frequency during the course of blood collection."

Further, in the platelet collecting apparatus 1 of this invention, the controller 13 possesses the function of circulating the plasma collected in the plasma collecting bag 25 at an accelerating rate to the centrifugal separator 20 and the function of changing the rotational frequency of the rotor 142 in conformity with the speed at which the plasma is circulated by the function of causing this accelerating circulation. The former function is called an accelerated plasma circulating function and the latter function is called a function of controlling rotor's rotational frequency during plasma circulation.

The platelet collecting apparatus 1 of the illustrated embodiment is endowed with the function of controlling the rotor's rotational frequency during blood collection, the accelerated plasma circulating function, and the function of controlling the rotor's rotational frequency during plasma circulation.

To be more specific, the platelet collecting apparatus 1 includes a platelet collecting circuit 2 and this platelet collecting circuit 2 comprises the centrifugal separator 20 mentioned above; the first line 21 for connecting a blood collection needle 29 or the connecting part of a blood collecting device (not shown) to the inlet 143 of the centrifugal separator 20; the second line 22 connected to the outlet 144 of the centrifugal separator 20; a third line 23 connected to the first line 21 for the purpose of injecting an anticoagulant; the plasma collecting bag 25 possessing a first tube 25a connected to the point falling halfway along the length of the first line 21 and a second tube 25b connected to the second line 22; and the platelet collecting bag 26 connected to the second line 22.

The platelet collecting apparatus 1 is further furnished with the centrifugal separator driving unit 10 for rotating the rotor 142 of the centrifugal separator 20; the blood delivering pump 11 intended to serve the first line 21; a liquid delivering pump 12 intended to serve the third line 23; a plurality of flow path switching means 81, 82, 83, 84, 85, and 86 intended to switch the flow path of the platelet collecting circuit 2; and the controller 13 intended to control the centrifugal separator driving unit 10, the blood delivering pump 11, the liquid delivering pump 12, and the plurality of flow path switching means 81~86.

The platelet collecting circuit 2 will be described in detail below.

This platelet collecting circuit 2 is a circuit intended to collect platelets alone or jointly with plasma. This platelet collecting circuit 2 is furnished with such a blood collecting device as the blood collection needle 29 or a connecting part to a blood collecting device possessing a blood collection needle or a blood pool connecting part (connecting part of a blood collecting device); the first line 21 (a blood collecting and blood returning line) intended to interconnect the blood collection needle or the blood collecting device connecting part and the inlet 143 of the centrifugal separator 20 and provided with a blood delivering pump tube 21g; the second line intended to interconnect the outlet 144 of the centrifugal separator 20 and the first line 21; the third line 23 (an anticoagulant injecting line) connected to the neighborhood of the blood collection needle 29 of the first line 21 and provided with a liquid delivering pump tube 23a; the plasma collecting bag 25 possessing the first tube 25a connected to a branching connector 21f positioned nearer to the blood collection needle side than to the blood delivering pump tube 21g of the first line 21 and the second tube 25b connected to the second line 22; a platelet collecting bag 26 provided with a third tube 26a connected to the second line 22; and a buffy coat collecting bag 27 provided with a fourth tube 27a connected to the second line 22. The platelet collecting circuit 2 may use a connecting part (such as, for example, a needle made of metal or synthetic resin) intended to be connected to such a blood pool as the blood bag in the place of the blood collection needle.

As the blood collection needle 29, a metallic hollow needle known to the art is used. The first line 21 includes a blood collection needle side part 21a connected to the blood collection needle 29 and a centrifugal separator side part 21b connected to the inlet 143 of the centrifugal separator 20. The blood collection needle side part 21a is formed of a plurality of tubes made of soft resin. The blood collection needle side part 21a is provided with a branching connector 21c for connection to the third line 23; a chamber 21d for removal of bubbles and microaggregates; a branching connector 21e for connection to the second line 22; and the branching connector 21f for connection to the first tube 25a of the plasma collecting bag 25 as reckoned from the blood collection needle side onward. The chamber 21d is connected to a filter 21i pervious to gas and impervious to microbes. The centrifugal separator side part 21b is provided with the blood drawing pump tube 21g connected to the branching connector 21f for connection to the first tube 25a and formed in the neighborhood of the branching connector 21f.

The second line 22 has one end thereof connected to the outlet 144 of the centrifugal separator 20 and the other end thereof connected to the branching connector 21e of the first line 21. The second line 22 is provided with a branching connector 22a for connection to the second tube 25b of the plasma collecting bag 25 and the third tube 26a of the platelet collecting bag 26; a branching connector 22c for connection to a tube provided with a pressure-sensitive filter 22f; and a branching connector 22d for connection to the fourth tube 27a of the buffy coat collecting bag 27 as reckoned from the centrifugal separator side onward.

The third line 23 has one end thereof connected to the branching connector 21c of the first line 21. The third line 23 is provided with the liquid delivering pump tube 23a, a foreign matter removing filter 23b; a bubble removing chamber 23c; and a connecting needle 23d for use with the anticoagulant container as reckoned from the branching connector 21c side onward.

The plasma collecting bag 25 is provided with the first tube 25a connected to the branching connector 21f positioned nearer to the blood collection needle side than to the blood delivering pump tube 21g of the first line 21 and the second tube 25b connected to the branching connector 22a of the second line 22. The platelet collecting bag 26 is provided with the third tube 26a connected to the branching connector 22a of the second line 22. The buffy coat collecting bag 27 is provided with the fourth tube 27a connected to the branching connector 22d of the second line 22.

Figure 2:
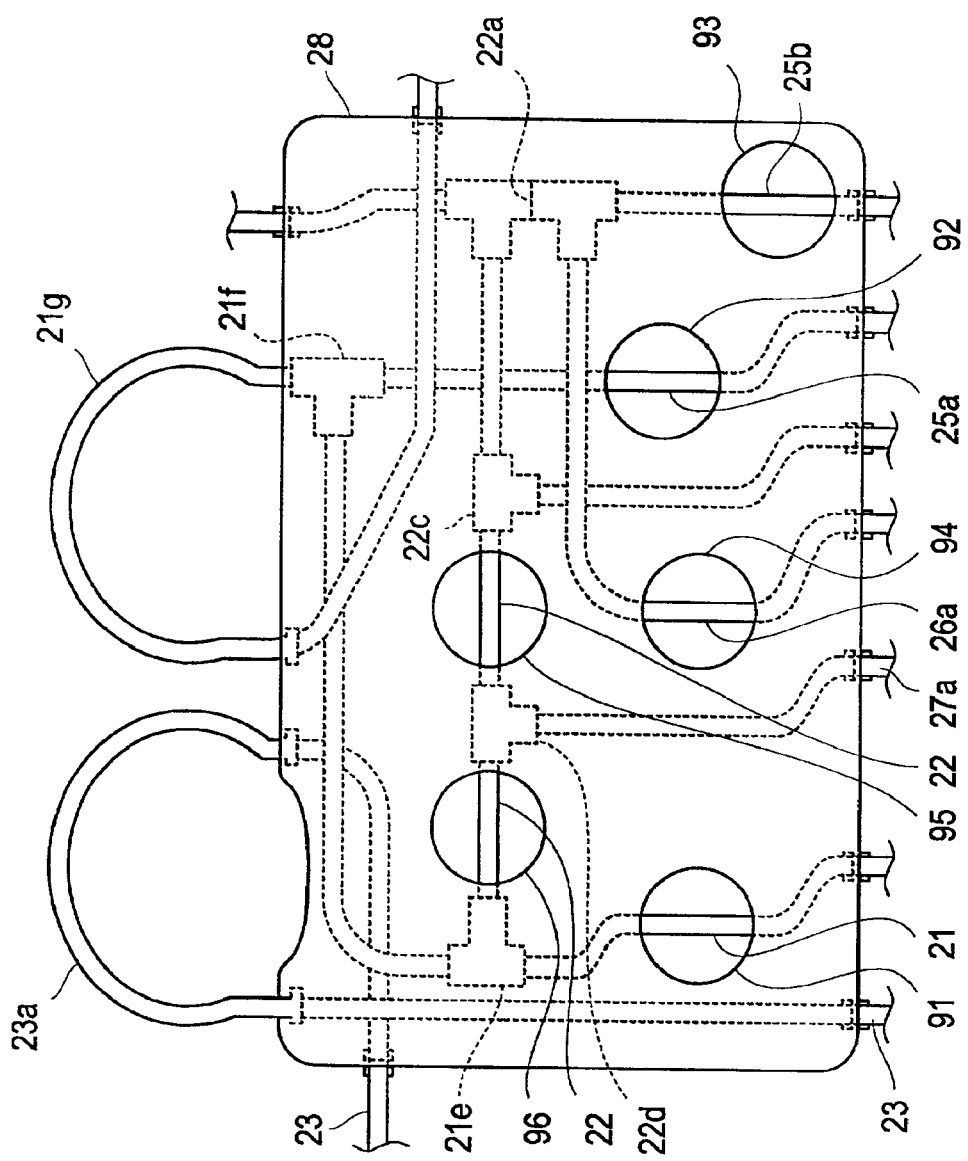
FIG. 2 is a plan view illustrating a cassette housing for the platelet collecting circuit shown in FIG. 1.

The main components of the platelet collecting circuit 2 are assembled in a cassette as illustrated in FIG. 2. The platelet collecting circuit 2 is provided with a cassette housing 28 for partially containing and partially retaining all the lines (the first, second, and third lines 21, 22, and 23) and all the tubes (the first, second, third, and fourth tubes 25a, 25b, 26a, and 27a). In other words, they are partially fixed in the cassette housing 28. To the cassette housing 28, the opposite ends of the blood delivering pump tube 21g and the opposite ends of the liquid delivering pump tubes 23a are fixed. The pump tubes 21g and 23a each project from the cassette housing 28 in the shape of a loop corresponding to the shape of the relevant roller pump. The blood delivering and liquid delivering pump tubes 21g and 23a, therefore, are each enabled to be easily attached to the relevant roller pump.

The cassette housing 28 is further provided with a plurality of openings positioned in the interior of the cassette housing 28. Specifically, the cassette housing 28 is provided with a first opening 91 exposing the first line 21 at a position nearer to the blood collection needle side than to the blood delivering pump tube 21g and permitting ingress of the first flow path switching means 81 as well; a second opening 92 exposing the first tube 25a of the plasma collecting bag 25 and permitting ingress of the second flow path switching means 82 as well; a third opening 93 exposing the second tube 25b of the plasma collecting bag 25 and permitting ingress of the third flow path switching means 83 as well; a fourth opening 94 exposing the third tube 26a of the platelet collecting bag 26 and permitting ingress of the fourth flowpath switching means 84 as well; a fifth-opening 95 exposing the second line 22 at a position nearer to the centrifugal separator side (on the upstream side) than to the connector 22d interconnecting the second line 22 and the fourth tube 27a of the buffy coat collecting bag 27 and permitting ingress of the fifth flow path switching means 85 as well; and a sixth opening 96 exposing the second line 22 positioned between the connector 21e interconnecting the first line 21 and the second line 22 and the connector 22d and permitting ingress of the sixth flow path switching means 86.

The branching connectors 21e, 21f, 22a, 22c, and 22d are fixed to the inner surface of the cassette housing 28. Near the lateral faces of the cassette housing 28 are disposed reinforcing tubes which are intended to retain those lines and tubes which project from the lateral faces of the housing 28 and preventing them from being bent in the housing part. The cassette housing 28 has the shape of a box capable of containing therein the part indicated with a broken line in FIG. 2. The cassette housing 28 is formed of such synthetic resin as possesses a certain degree of rigidity.

The platelet collecting apparatus 1 is furnished with a cassette housing mounting part (not shown). When the cassette housing 28 is attached to the cassette housing mounting part, the lines and the tubes which are exposed through the openings 91~96 of the cassette housing 28 are automatically fitted to the corresponding flow path switching means 81~86. As a result, the platelet collecting circuit 2 can be easily attached to the platelet collecting apparatus 1 and the preparations for collecting platelets can be quickly effected. In the platelet collecting apparatus 1, the two pumps 11, 12 are disposed in proximity to the cassette housing mounting part. Thus, the attachment of the pump tubes 21g, 23a exposed from the cassette housing 28 to the corresponding pumps 11, 12 can be carried out easily.

Figure 3:
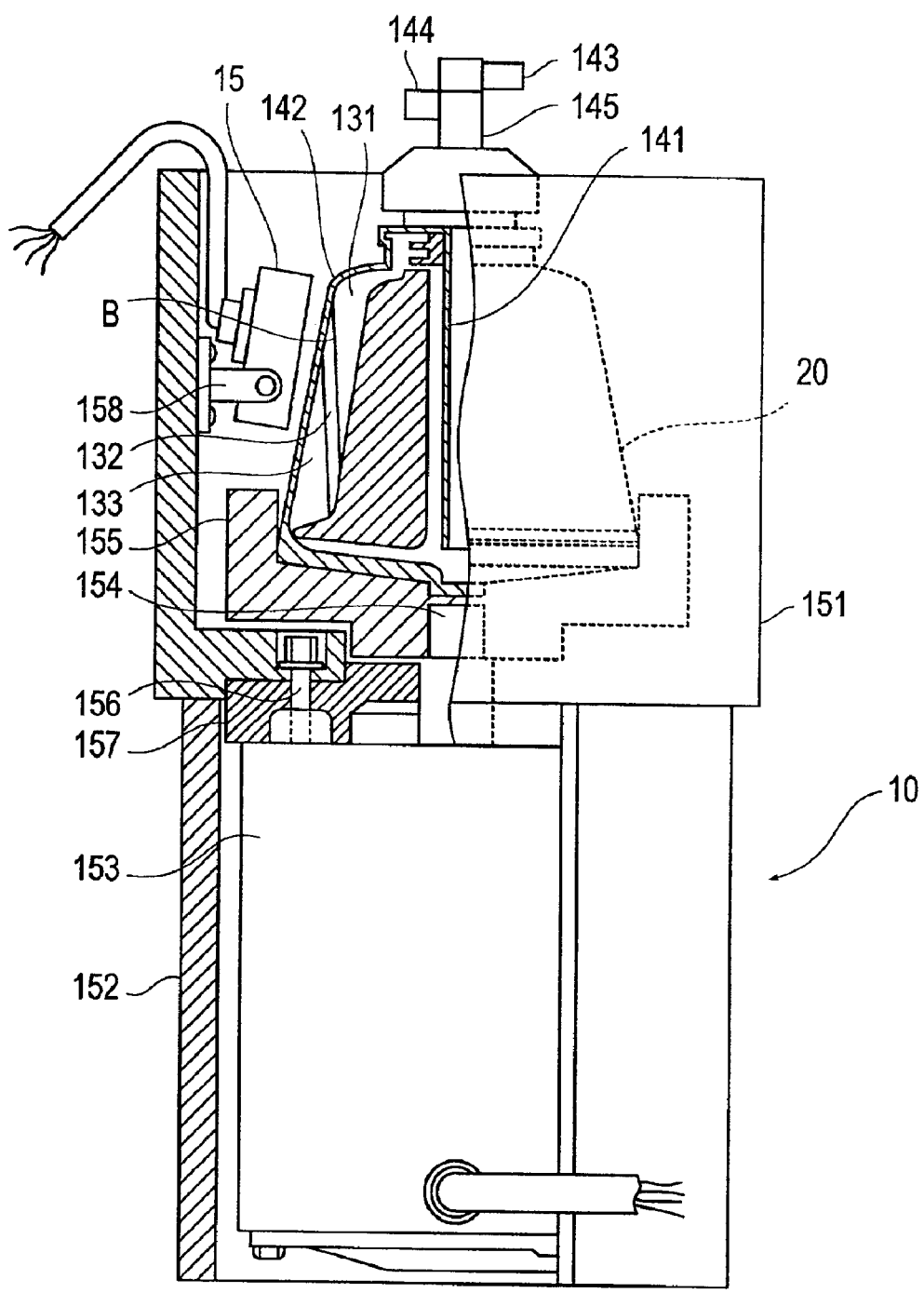
FIG. 3 is a partially cutaway cross section illustrating the state in which a driving unit is inserted in a centrifugal separator used in the platelet collecting circuit.

The centrifugal separator 20 is generally called a centrifugal bowl and is disposed in the platelet collecting circuit 2 for the purpose of separating blood components by virtue of centrifugal force. The centrifugal separator 20, as illustrated in FIG. 3, is furnished with a tubular body 141 extending in the vertical direction and having the inlet 143 formed in the upper end thereof and the hollow rotor 142 sealed to prevent leakage of liquid from an upper part 145 and rotated around the tubular body 141. The rotor 142 is furnished with a flow path (a blood storing space) formed in the bottom part thereof and along the inner face of the peripheral wall thereof. The outlet 144 is formed so as to communicate with the upper part of this flow path. The inner volume of this rotor 142, for example, is in the approximate range of 100~350 ml.

The rotor 142 is rotated under predetermined or computed fixed centrifugal conditions (speed of rotation and duration of rotation) by the centrifugal separator driving unit 10. By the centrifugal conditions, the pattern of blood separation in the rotor 142 (such as, for example, the number of blood components) can be set. In the present embodiment, the centrifugal conditions are so set as to separate the blood inside the flow path of the rotor 142 into a plasma layer 131, a buffy coat layer 132, and a erythrocyte layer 133 as reckoned from the inner layer outward as illustrated in FIG. 3.

Figure 4:
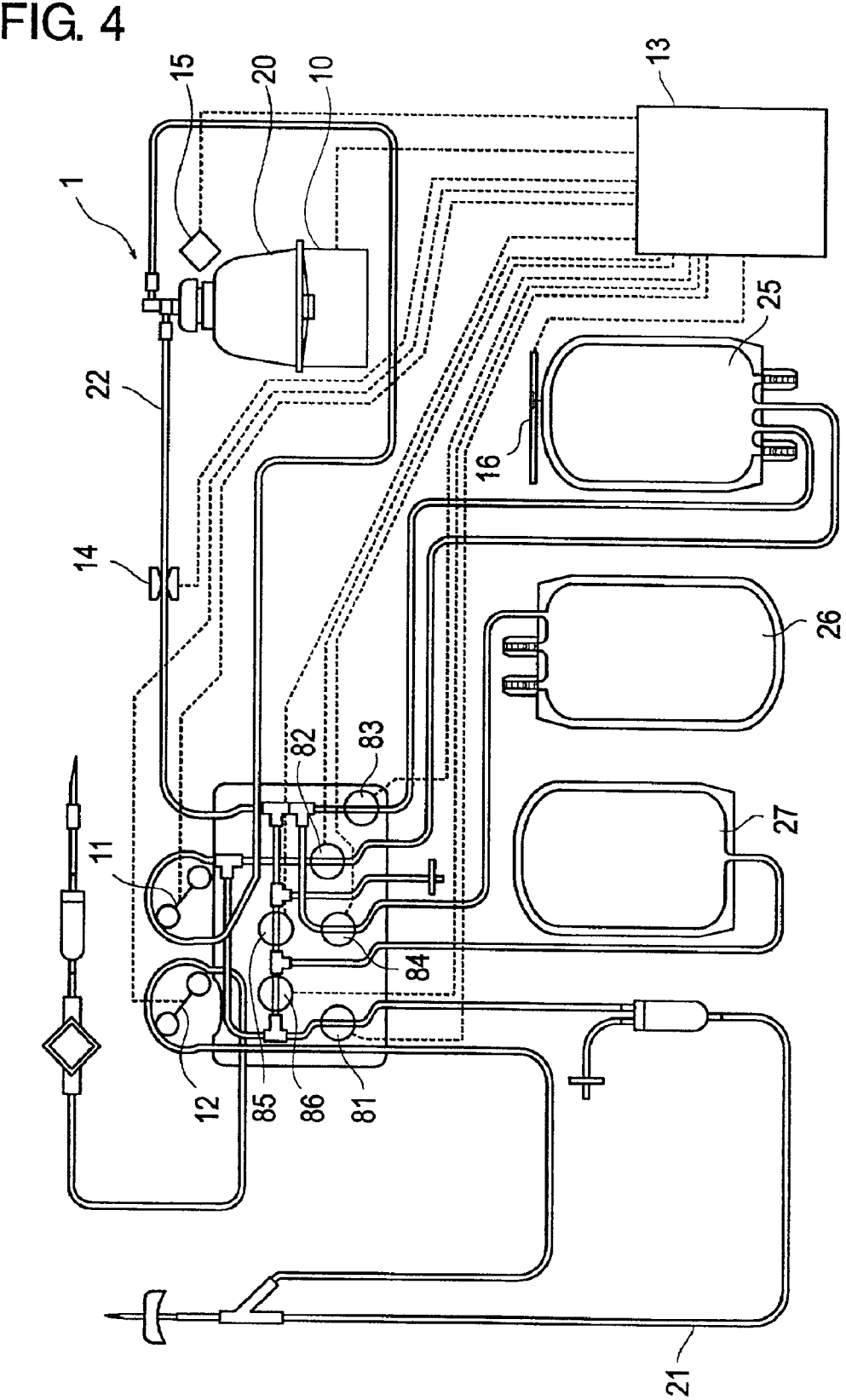
FIG. 4 is an artist's conceptual drawing illustrating one preferred embodiment of the platelet collecting apparatus according to this invention.

With reference to FIG. 4, the platelet collecting apparatus 1 is furnished with the centrifugal separator driving unit 10, the blood delivering pump 11 intended to serve the first line 21, the liquid delivering pump 12 intended to serve the third line 23, the plurality of flow path switching means 81 86, and the controller 13. The platelet collecting apparatus 1 is further furnished with a turbidity sensor 14 attached to the second line 22 at a position nearer to the centrifugal separator side (in the upstream side) than to the connector 22a interconnecting the second tube 25b and the second line 22; an optical sensor 15 attached to the upper part of the centrifugal separator 20; and a weight sensor 16 for detecting the weight of the plasma collecting bag 25.

The flow path switching means 81~86 are invariably connected to the controller 13 and their switching motions are controlled by the controller 13. The turbidity sensor 14, the optical sensor 15, and the weight sensor 16 are also electrically connected to the controller 13. The signals of detection emitted from the weight sensor 16, the optical sensor 15, and the turbidity sensor 14 are entered into the controller 13 from time to time. The controller 13 controls the rotation, suspension, and direction of rotation (normal rotation/reverse rotation) of the pumps 11, 12 and, when necessary, controls the switching motions of the flow path switching means 81~86 and the operation (rotation of the rotor) of the centrifugal separator driving unit 10 based on the signals from the sensors 14, 15, and 16.

The first flow path switching means 81 is installed for the purpose of switching the first line 21 at a position nearer to the blood collection needle side than to the blood delivering pump tube 21g. The second flow path switching means 82 is installed for the purpose of switching the first tube 25a of the plasma collecting bag 25. The third flow path switching means 83 is installed for the purpose of switching the second tube 25b of the plasma collecting bag 25. The fourth flow path switching means 84 is installed for the purpose of switching the third tube 26a of the platelet collecting bag 26. The fifth flow path switching means 85 is installed for the purpose of switching the second line 22 at a position nearer to the centrifugal separator side (on the upstream side) than to the connector 22d interconnecting the second line 22 and the fourth tube 27a of the buffy coat collecting bag 27. The sixth flow path switching means 86 is installed for the purpose of switching the second line 22 at a position between the connector 21e interconnecting the first line 21 and the second line 22 and the connector 22d (at the position on the downstream side of the connector 22d). The flow path switching means 81~86 are provided with insertion parts for permitting insertion of lines or tubes. This insertion parts are each provided with a clamp operated with such a drive source as solenoid, electric motor, or cylinder (using hydraulic pressure or pneumatic pressure). Specifically, this clamp is preferred to be a pneumatic cylinder clamp which is operated with pneumatic pressure. The clamps which serve the flow path switching means 81~86 are operated based on the signals issuing from the controller 13.

The centrifugal separator driving unit 10 is furnished as illustrated in FIG. 3 with a housing 151 for containing the centrifugal separator 20; a shank 152; a motor 153 serving as a drive source; and a discoid standing base 155 for retaining the centrifugal separator 20. The housing 151 is mounted on the shank 152 and fixed thereto. To the lower face of the housing 151, the motor 153 is fixed with a bolt 156 through the medium of a spacer 157. In the leading end part of the rotary shaft 154 of the motor 153, the standing base 155 is fitted so as to rotate coaxially and integrally with a rotating shaft 154. In the upper part of the standing base 155, a depressed part capable of admitting the bottom part of the rotor 142 in snug fit is formed. The upper part 145 of the centrifugal separator 20 is fixed to the housing 151 with a fixing member not shown in the diagram. When the motor 153 is driven, the standing base 155 and the rotor 142 fixed thereto are rotated at a rotational frequency in the range of 3,000~6,000 rpm.

On the inner wall of the housing 151, the optical sensor 15 is set and fixed with an anchoring member 158. The optical sensor 15 optically detects the position of the boundaries of the blood components separated in the centrifugal separator 20 (such as, for example, the boundary B between the plasma layer 131 and the buffy coat layer 132 and the boundary between the buffy coat layer 132 and the erythrocyte layer 133). This sensor 15 is furnished with a light source for emitting light toward the part of the shoulder of the centrifugal separator 20 and a light receiving part for receiving the light reflected and returned from the centrifugal separator 20. The light source is formed by having such light emission elements as LED or laser laid out in series and the light receiving part is formed by having light receiving elements laid out in series. The light receiving part receives the light emitted from the light emitting elements and reflected by the blood components and effects photoelectric conversion of the amount of the received light. Since the lights reflected by the separated blood components (for example, the plasma layer 131 and the buffy coat layer 132) are varied in intensity, the position which corresponds to the light receiving element revealing a change in the amount of light received is detected as the position of the boundary B. To be more specific, the arrival of the buffy coat layer 132 at the part passing the light is detected based on the difference between the amount of light received when the light passing part of the centrifugal separator 20 is filled with a transparent liquid (plasma or water) and the amount of light received when the light passing part is filled with the buffy coat layer 132. The position for detecting the buffy coat layer 132 is adjusted by varying the position of passage of light in the centrifugal separator 20. Once the position for passing light is decided, this position is fixed.

The turbidity sensor 14 detects the turbidity of a liquid flowing in the second line 22 and emits a voltage value corresponding to the detected turbidity. To be specific, the turbidity sensor 14 emits a small voltage value when the turbidity is high and a large voltage value when the turbidity is low.

As the blood delivering pump 11 to which the blood delivering pump tube 21g of the first line 21 is attached and the liquid delivering pump 12 to which the liquid delivering pump tube 23a of the third line 23 is attached, such pumps as roller pumps or peristaltic pumps which are not intended to contact blood are advantageously used. As the blood delivering pump 11 (the blood pump), a pump capable of delivering blood in any selected direction may be used. To be specific, the use of a roller pump capable of producing normal rotation and reverse rotation is now in vogue.

Figure 5:
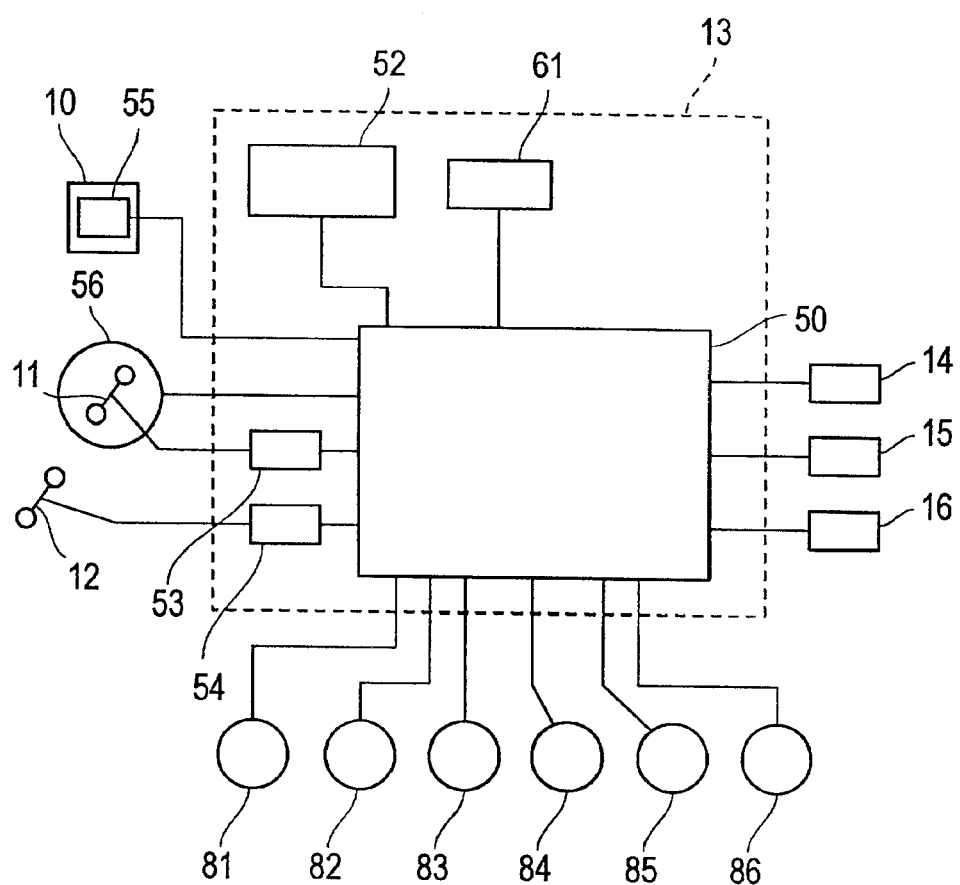
FIG. 5 is a schematic block diagram illustrating a controlling system for the platelet collecting apparatus of this invention.
Figure 6:
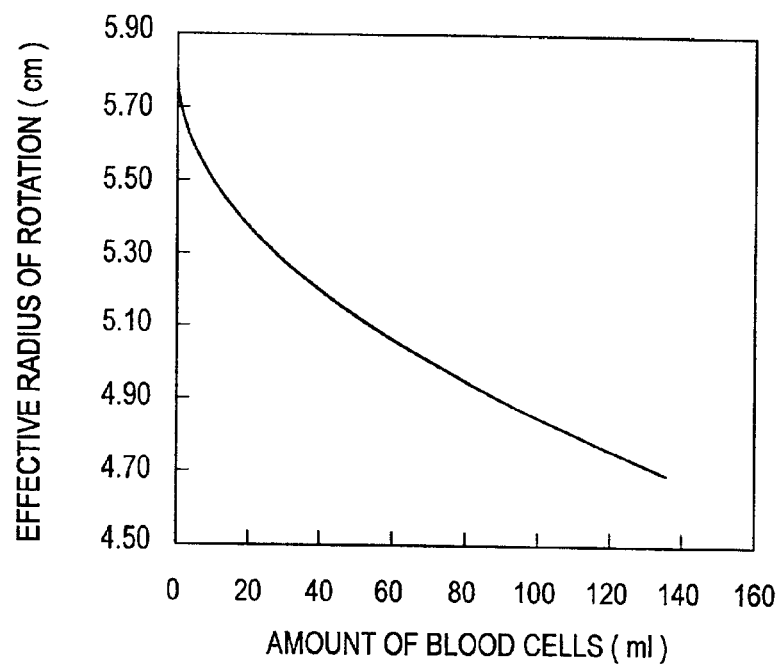
FIG. 6 is a graph showing the relation between the amount of the blood cells collected and the effective radius of rotation, existing in the case of using a standard bowl type centrifugal separator.

With reference to FIG. 5, the controller 13 is furnished with a control device 50 for governing the overall control and the processing operation of the platelet collective apparatus 1; a pump controller 53 intended to serve the blood delivering pump 11; a pump controller 54 intended to serve the liquid delivering pump 12; and an input device 61 for entering a hematocrit value. The blood delivering pump 11 and the liquid delivering pump 12 are connected electrically to the control device 50 through the medium of the pump controllers 53, 54. To the blood delivering pump 11, an operating amount detecting device 56 for detecting the amount of operation of the pump is attached. The operating amount detecting device 56 is connected electrically to the control device 50. As the operating amount detecting device 56, a means capable of detecting the amount of rotation of the roller pump may be used. To be specific, a rotary encoder may be advantageously used. The control device 50 is further connected electrically to a drive controller 55 of the centrifugal separator driving unit 10.

To the control device 50, a memory device 52 which has memorized the amount of blood delivered per unit amount of operation of the blood delivering pump 11 is connected. The controller 13 computes the rotational frequency of the rotor of the centrifugal separator 20 (the number of revolutions of the rotor during the blood collection) at the end of the first round of blood collection by utilizing the memorized amount of blood delivered per unit amount of operation of the blood delivering pump 11 and the hematocrit value injected from the input device 61. This function will be referred to hereinafter as the function of calculating the rotational frequency of rotor during the blood collection. The control device 50 is further endowed with a function of controlling the rotational frequency of the rotor 142. This function of controlling the rotational frequency of the rotor consists in successively increasing the rotational frequency of the rotor 142 to the rotational frequency of the rotor during the blood collection computed by the function of calculating the rotational frequency of the rotor during the blood collection, depending on the amount of blood flowing in the centrifugal separator 20.

The rotational frequency of the centrifugal separator 20 is gradually increased from the initial rotational frequency selected from the range of 3,000~5,000 rpm till the prescribed rotational frequency (the rotational frequency of the rotor during the blood collection) at the end of the first round of blood collection, depending on the amount of blood cells (the volume of erythrocytes) in the centrifugal separator. The rotational frequency at the end of the first round of blood collection is selected from the range of 4,500~5,500 rpm. The rotational frequency at the end of the first round of blood collection is set in accordance with the hematocrit value of the donor. When the hematocrit value of the donor is smaller than the standard hematocrit value (35~45%, preferably 40%), the rotational frequency at the end of the first round of blood collection is set at a lower level than the rotational frequency of the standard hematocrit value at the end of the first round of blood collection. When the hematocrit value of the donor is large, it is set at a higher level. The rotational frequency at the end of the first round of blood collection is computed in accordance with the following formula (1). The control device 50 memorizes this formula (1) and computes the rotational frequency at the end of the first round of blood collection by using this formula.

$$w = w_0 - k \times \{H_{std} - H_d/(1+ACD)\} \quad (1)$$

wherein
w=the rotational frequency at the end of the first round of blood collection (rpm)
$w_0$=the rotational frequency at the end of the first round of blood collection (rpm) relative to the standard hematocrit value
k=coefficient (0.01~15)
$H_{std}$=the standard hematocrit value (%)
$H_d$=the donor's hematocrit value (%)
ACD=amount of anticoagulant/amount of blood The control device 50 may be endowed with a function of computing the ratio of increase in the rotational frequency of the rotor per unit time. That is to say, it may be endowed with a function of computing the time required for the set amount of blood to complete entering the centrifugal separator 20 based on the memorized amount of blood delivered per unit amount of operation of the blood delivering pump 11 and the amount of blood set for entry into the centrifugal separator 20 and then computing the ratio of increase of the rotational frequency of the rotor per unit time from the initial rotational frequency of the rotor to the rotational frequency at the end of the first round of blood collection computed in accordance with the formula (1). The ratio of increase of the rotational frequency of the rotor can be computed in accordance with the following formula, for example.

Ratio of increase of rotational frequency=(rotational frequency of the rotor during blood collection−initial rotational frequency of the rotor)/time for arrival The function fulfilled by the platelet collecting apparatus 1 of this invention in controlling the rotational frequency of the rotor during blood collection consists in increasing the rotational frequency of the rotor 142 successively to the rotational frequency of the rotor during blood collection, depending on the amount of blood entering the centrifugal separator 20, i.e. depending on the increase in the amount of inflow into the centrifugal separator 20, namely depending on the increase in the amount of blood stored in the centrifugal separator 20.

When the blood delivering pump 11 is such a roller pump as illustrated in FIG. 4 and FIG. 5, the amount of inflow into the centrifugal separator 20 is computed as the product of the total rotational frequency of the pump 11 detected by the operating amount detecting device 56 multiplied by the memorized amount of blood delivered per unit amount of operation of the blood delivering pump 11. When the blood delivering pump 11 is a peristaltic pump, the amount of inflow into the centrifugal separator 20 is computed as the product of the time of operation of the pump multiplied by the amount of blood delivered per unit amount of operation of the blood delivering pump 11.

The centrifugal separator 20 is provided with the inlet port 143 and the outlet port 144 and intended to separate the collected whole blood into blood components. The present inventors have acquired a knowledge that the packing density of blood cells within the centrifugal separator 20 is made uniform by increasing the rotational frequency of the centrifugal separator 20 in conformity with the amount of blood cells collected in the centrifugal separator 20.

On the blood cells which have been collected in the centrifugal separator 20, the centrifugal force Fc computed by the following formula (2) is acting.

$$Fc = \{2\pi d^3(\rho s - \rho f)r\omega^2\}/3 \qquad (2)$$

wherein
d=the diameter of blood cells
ρs=the density of blood cells
ρf=the density of liquid in which blood cells produce a rotational motion
r=the effective radius of rotation of the rotational motion of the blood cell
ω=the angular velocity of the rotational motion of the blood cells The blood cells which are collected in the centrifugal separator 20 are successively separated and packed by the centrifugal force Fc in the direction of radius in the centrifugal separator 20. The effective radius r of rotation for the blood cells being collected in the centrifugal separator 20 continues to decrease in accordance with the amount of blood cells being collected.

For the purpose of imparting the same centrifugal force Fc constantly to the blood cells collected in the centrifugal separator 20 and making the packing density of blood cells uniform, therefore, it suffices to increase the angular velocity ω or the frequency of centrifugal rotation, in conformity with the amount of blood cells to be collected.

Figure 7:
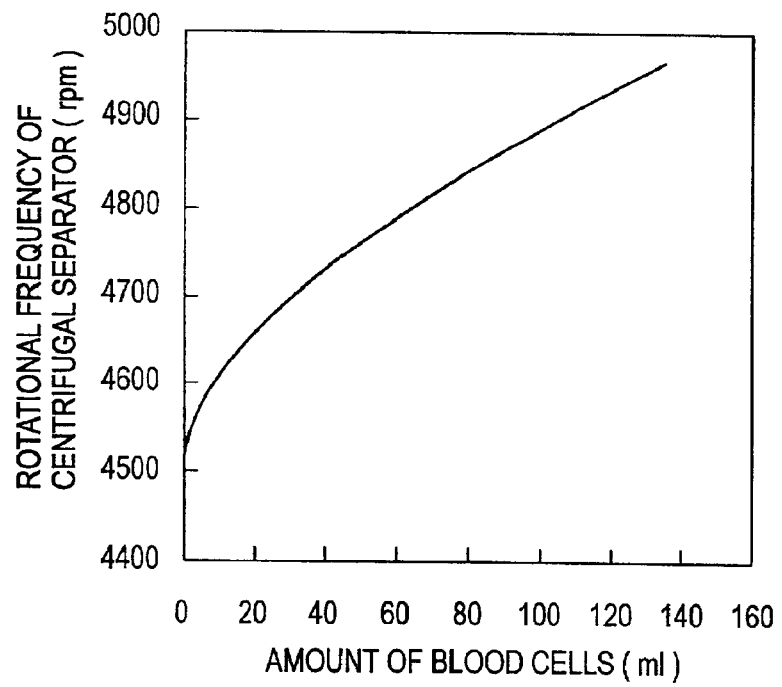
FIG. 7 is a graph showing the change in the rotational frequency of the centrifugal separator necessary for imparting constantly the same centrifugal force to blood cells being collected, existing in the case of using a standard bowl type centrifugal separator.

When the centrifugal separator 20 to be used is a bell-shaped bowl, for example, the effective radius of rotation r for the blood cells to be collected decreases in accordance as the amount of blood cells to be collected increases. For the purpose of imparting the same centrifugal force Fc constantly to the blood cells collected in the centrifugal separator 20 and making the packing density of blood cells uniform, therefore, it suffices to increase the centrifugal rotational frequency in conformity with the amount of blood cells to be collected as illustrated in FIG. 7. A difference occurs between the centrifugal force Fc exerted on the blood cells initially separated and collected and the centrifugal force Fc exerted on the blood cells to be subsequently separated and collected and makes the packing density of blood cells ununiform unless the centrifugal force Fc is increased in conformity with the amount of blood cells collected in the centrifugal separator 20. This fact forms the cause for giving rise to dispersion in the separation of blood cells and the collection of platelets.

According to the platelet collecting apparatus 1 of this invention, the whole blood from the donor, after adding thereto the anticoagulant at a stated ratio, is delivered by the blood delivering pump 11 and collected in the centrifugal separator 20 which has the rotational frequency thereof increase in conformity with the amount of blood cells to be collected therein until the volume of erythrocytes in the centrifugal separator 20 reaches a stated level. Then, the rotational frequency of the rotor during the collection of blood in the centrifugal separator 20 is varied with the hematocrit value of the blood.

By varying the rotational frequency of the rotor of the centrifugal separator 20 during the course of blood collection in conformity with the hematocrit value, the effect of the centrifugal force is enabled to assume a fixed value constantly without relying on the hematocrit value of the blood. That is to say, the whole blood from the donor, after adding thereto the anticoagulant at a stated ratio, is delivered by the blood delivering pump 11 and separated and collected in the centrifugal separator 20 which has the rotational frequency thereof increase in conformity with the amount of blood cells to be collected therein until the volume of erythrocytes in the centrifugal separator 20 reaches a stated level. The time t which is required for the volume to reach the stated level depends on the flow rate of the blood delivering pump 11 and the hematocrit value of the donor.

Generally, the effect of the centrifugal force is expressed by the following formula.

Effect of centrifugal force=Centrifugal force $(Fc)$×time $(t)$

The time (t) in this case is computed by the following formula (3).

Time (t)={(stated amount of collected blood cells)/(hematocrit value)}/(flow rate of the pump) (3)

For the purpose of imparting the same effect of centrifugal force constantly to the blood cells separated and collected in the centrifugal separator 20 without relying on the hematocrit value of the donor, therefore, it suffices to vary the centrifugal force or the centrifugal rotational frequency in conformity with the hematocrit value of the donor.

When the flow rate of the blood delivering pump 11 is fixed and the hematocrit value of the donor is lower than a certain standard value, for example, the time t required for the volume of erythrocytes in the centrifugal separator 20 to reach a stated level becomes long as compared with the case resorting to the standard hematocrit value. For the purpose of imparting to the blood cells collected in the centrifugal separator 20 the same effect of centrifugal force as when the hematocrit value is the standard value, therefore, it becomes necessary to decrease the centrifugal rotational frequency in conformity with the hematocrit value. Conversely, when the hematocrit value of the donor is higher than the standard value, the time t required for the volume of erythrocytes in the centrifugal separator 20 to reach the stated level becomes short as compared with the case of resorting to the standard hematocrit value. For the purpose of imparting to the blood cells collected in the centrifugal separator 20 the same effect of centrifugal force as when the hematocrit value is the standard value, therefore, it becomes necessary to increase the centrifugal rotational frequency in conformity with the hematocrit value. In short, since the time for terminating the blood collection (in other words, when the stated amount of blood has flowed in the centrifugal separator 20 or when the volume of erythrocytes has reached the stated level) is reached early when the hematocrit value is large, the time for rotation becomes insufficient and the separation becomes deficient when the centrifugal rotational frequency is kept set at a fixed level. Conversely, since the time for terminating the blood collection is reached late when the hematocrit value is small, the time for rotation becomes excessive and the phenomenon of packing seems to occur when the centrifugal rotational frequency is kept set at a fixed level. Incidentally, the amount of the blood is detected by the amount of operation of the blood delivering pump 11 such as, for example, the amount of rotation of the roller pump.

When the rotational frequency of the centrifugal separator 20 is not varied in conformity with the hematocrit value of the donor as described above, a difference arises between the effect of the centrifugal force exerted on the blood of a small hematocrit value and the effect of the centrifugal force exerted on the blood of a large hematocrit value. As a result, the packing density of the blood cells in the centrifugal separator 20 is caused to depend on the hematocrit value of the donor and the dispersion due to the hematocrit value of the donor is inevitably exerted on the separation of leukocytes and the collection of platelets which will be carried out subsequently.

The platelet collecting apparatus 1 of this invention is further endowed with a function of controlling the rotational frequency of the rotor during the circulation of plasma which varies the rotational frequency of the rotor in conformity with the speed of circulation of the plasma being circulated by the function of accelerating circulating the plasma. That is to say, the platelet collecting apparatus 1 of this invention is endowed with a function of simultaneously increasing the resistance generated by the motion of plasma and the centrifugal force when the plasma is allowed to produce a motion in the interstices between the adjacent blood cells (in other words, when the circulation of the plasma is started) after the whole blood from the donor, subsequently to the addition thereto of the anticoagulant at a stated ratio, has been delivered by the blood delivering pump 11 and collected in the centrifugal separator 20 which has the rotational frequency thereof increase or decrease in conformity with the amount of blood cells to be collected therein and/or the hematocrit value until the volume of erythrocytes in the centrifugal separator 20 reaches a stated level. By simultaneously increasing the resistance generated by the motion of the plasma and the centrifugal force during the motion of plasma in the interstices between the adjacent blood cells, it is made possible to enhance the separation of blood cells in the centrifugal separator 20.

The blood cells collected in the centrifugal separator 20 are exposed to the force generated outwardly in the radial direction of the interior of the centrifugal separator 20 by the centrifugal force Fc indicated by the formula (2). By causing the plasma to move in the interstices between the adjacent blood cells, the blood cells are exposed to the force generated inwardly in the radial direction of the interior of the centrifugal separator 20 by the resistance generated by the motion of the plasma. The resistance Fd in this case is computed in accordance with the following formula (4).

$$Fd=(\rho v^2 S C_D)/2 \qquad (4)$$

wherein
  $\rho$=the density of plasma
  $v$=the speed of motion of plasma
  $S$=the frontal projected area of blood cells
  $C_D$=the coefficient of resistance of sphere The blood cells collected in the centrifugal separator 20, therefore, are moved under the centrifugal force Fc generated outwardly relative to the radial direction and the resistance Fd generated inwardly. The individual blood cells are caused to produce a motion which varies with the density ps and the diameter d. Since erythrocytes and leukocytes differ in density ps and diameter d from platelets, all of them are destined to produce different motions. As a result, the separation of blood cells is carried out in the centrifugal separator 20. When the resistance Fd generated by the motion of plasma and the centrifugal force Fc are increased simultaneously at this time, the difference between the motion of platelets and the motion of leukocytes grows greater and the separation between platelets and leukocytes proceeds more efficiently.

Figure 8:
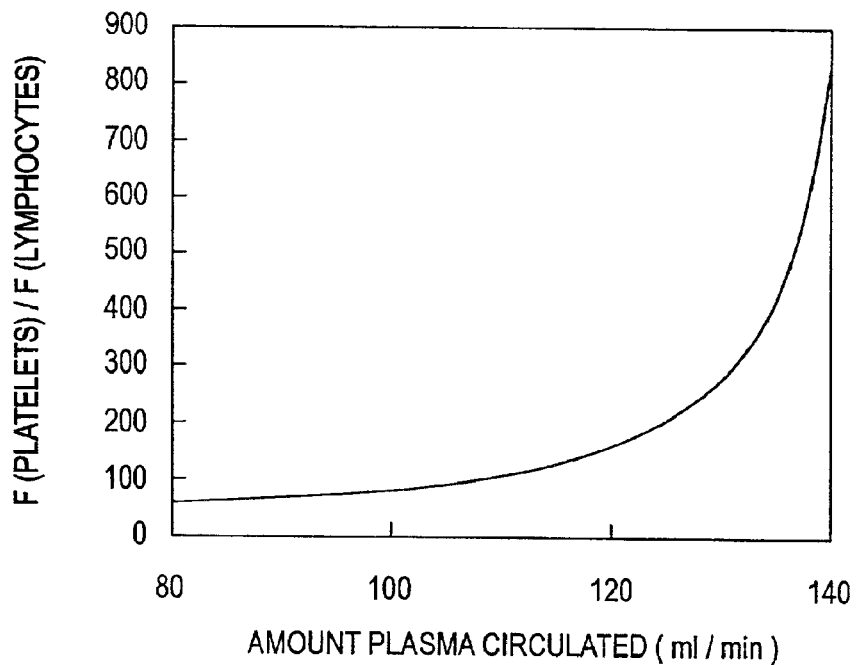
FIG. 8 is a graph showing the ratio of the force received by platelets to the force received by lymphocytes in leukocytes existing in the case of increasing the amount of plasma to be circulated and, at the same time, increasing the rotational frequency of the centrifugal separator, more specifically a graph showing the case in which blood is collected by using a standard bowl type centrifugal separator until the volume of erythrocytes in the centrifugal separator reaches 140 ml and thereafter the amount of plasma to be circulated is increased from 80 ml/min to 140 ml/min and, at the same time, the rotational frequency of the centrifugal separator is increased from 4,750 rpm to 5,400 rpm within a period of 30 seconds during the movement of the plasma in the interstices between the adjacent blood cells.

For example, such a bell-shaped bowl as illustrated in FIG. 3 is used as the centrifugal separator 20 and the amount of platelets to be circulated is increased from 80 ml/min to 140 ml/min and, at the same time, the centrifugal rotational frequency is increased from 4,750 rpm to 5,400 rpm over a period of 30 seconds during the motion of plasma in the interstices between the adjacent blood cells after the whole blood from the donor, subsequently to the addition thereto of the anticoagulant at a stated ratio, has been delivered by the blood delivering pump 11 and collected in the centrifugal separator 20 which has the rotational frequency thereof vary with the amount of blood cells to be collected therein and/or the hematocrit value until the volume of erythrocytes in the centrifugal separator 20 reaches a stated level (140 ml, for example). As a result, the ratio of the force "F (platelets)" exerted on platelets to the force "F (lymphocytes)" exerted on lymphocytes in leukocytes increases with the increase in the flow rate and the increase in the rotational frequency, namely with the elapse of time, as illustrated in FIG. 8. After the elapse of 30 seconds, this ratio reaches 800 times and the separation of platelets and lymphocytes efficiently proceeds.

In contrast, when the motion of plasma in the interstices between the adjacent blood cells is produced at a fixed rotational frequency of 4,750 rpm, for example, and at a fixed flow rate of 100 ml/min, for example, the ratio of the force "F (platelets)" exerted on platelets to the force "F (lymphocytes)" exerted on lymphocytes in leukocytes is about 150 times.

Also from this result, it can be understood that during the motion of plasma in the interstices between adjacent blood cells, the separation of blood cells in the centrifugal separator 20 can be enhanced by simultaneously increasing the resistance Fd generated by the motion of plasma and the centrifugal force Fc.

The controller 13 executes a plasma collection/accelerating circulation step at least one time, then a platelet collecting step, and subsequently a blood returning step. To be more specific, the plasma collection/accelerating circulation step comprises a plasma collecting step for collecting blood which has incorporated therein an anticoagulant, separating the collected blood, and collecting the separated plasma in the plasma collecting bag 25 and an accelerating plasma circulating step for causing the plasma collected in the plasma collecting bag 25 by the plasma collecting step to be circulated as accelerated to the centrifugal separator 20. The platelet collecting step is executed to introduce plasma into the centrifugal separator 20, expel platelets from the centrifugal separator 20, and collect the platelets in the platelet collecting bag 26 after completion of the plasma collection/accelerating circulation step. The blood returning step is executed to return the blood in the centrifugal separator 20 to the donor after the completion of the platelet collecting step. Every, except the last, round of the operation for collecting platelets is preferred to perform the buffy coat collecting step for causing emanation of buffy coat from the interior of the centrifugal separator 20 and collecting the emanating buffy coat in the buffy coat collecting bag 27 prior to the execution of the blood returning step. It is further preferred to perform the buffy coat returning step for returning the collected buffy coat to the interior of the centrifugal separator 20 prior to the execution of the subsequent plasma collecting step.

The operation of the platelet collecting apparatus 1 of this invention will be outlined below with reference to FIG. 9.

First, the blood of the donor is tested for hematocrit value and the hematocrit value thus obtained is injected through the input device 61 of the controller 13. The controller 13 computes the rotational frequency w at the end of the first round of blood collection (the rotational frequency during the blood collection) in accordance with the formula (1) using the introduced hematocrit value. The controller 13 computes the time elapsing between the time the operation of the blood delivering pump 11 is started (the start of blood collection) and the time the injection of the prescribed amount of blood into the centrifugal separator 20 is completed, particularly the volume of erythrocytes in the centrifugal separator 20 reaches a prescribed level. The memory device 52 continues to remember the amount of blood delivered per rotation of the blood delivering pump 11 which is formed of a roller pump. The controller 13 computes the ratio of increase of the rotational frequency of the rotor by using the rotational frequency w at the end of the first round of blood collection, the time required for the arrival, and the amount of blood delivered per rotation of the blood delivering pump 11. Optionally, the platelet collecting apparatus 1 may be further furnished with a measuring device for measuring the hematocrit value of the donor's blood and thereby enabled to compute the rotational frequency w at the end of the first round of blood collection based on the determined hematocrit value and omit the input of the hematocrit value.

The controller 13 starts the rotation of the rotor 142 at the initial rotational frequency (3,000~5,000 rpm). When the first round of blood collection (the plasma collecting step mentioned above) starts, the anticoagulant is added to the blood at a stated ratio. This fixed ratio is in the range of 1/8~1/20, specifically 1/10, based on the whole blood. The controller 13 rotates the blood delivering pump 11 so that the blood to which the anticoagulant has been added may flow at a stated flow rate. The stated flow rate is properly in the range of 20~90 ml/min, preferably 60 ml/min. The blood to which the anticoagulant has been added passes through the first line 21 and flows into the centrifugal separator 20 rotating at the initial rotational frequency. The controller 13 continues to increase the rotational frequency of the rotor 142 in accordance with the computed increasing ratio of the rotational frequency of the rotor. The blood which has been introduced into the centrifugal separator 20 is separated into plasma, buffy coat, and erythrocytes.

The controller 13 terminates the increase of the rotational frequency of the rotor, stops the blood delivering pump 11, and suspends the collection of blood at the time that the amount of blood delivered by the blood delivering pump 11 or the amount of blood introduced into the centrifugal separator 20 has reached a prescribed level, more specifically at the time that the volume of erythrocytes in the centrifugal separator 20 has reached a level in the range of 120~150 ml. The rotation of the rotor 142 is continued at the rotational frequency w existing at the end of the first round of blood collection. Optionally, the increase of the rotational frequency of the rotor may be terminated at the time that the rotational frequency w at the end of the first round of blood collection has been reached and the rotation of the rotor 142 may be retained thereafter at the rotational frequency w at the end of the first round of blood collection. The plasma which emanates from the centrifugal separator 20 is collected in the plasma bag 25.

The fact that the amount of blood to be delivered by the blood delivering pump 11 or the amount of blood introduced into the centrifugal separator 20 has reached the prescribed level means that the volume of erythrocytes in the centrifugal separator 20 has reached the prescribed level. The question whether the volume of erythrocytes in the centrifugal separator 20 has reached the prescribed level or not can be judged based on the hematocrit value, the ratio of increase of the anticoagulant, and the amount of blood delivered by the blood delivering pump 11. Specifically, the volume Vr of erythrocytes in the centrifugal separator 20 is computed in accordance with the following formula (5).

$$Vr = Hd/(1+ACD) \times 0.01 \times V \qquad (5)$$

wherein

Vr=the volume of erythrocytes in the centrifugal separator

Hd=the hematocrit value (%) of the donor

ACD=the ratio of amount of anticoagulant/amount of blood

V=the amount of blood delivered by the blood delivering pump

The amount of blood V delivered by the blood delivering pump 11 can be computed by using the amount of blood to be delivered per the unit amount of operation of the blood delivering pump 11 memorized in the memory device 52 (specifically, the amount of blood delivered per rotation of the roller pump) and the signal of detection of the amount of operation of the blood delivering pump 11 injected into the control device 50 (specifically, the total number of rotation of the roller pump detected by the rotary encoder 56).

Then, the accelerating circulation of plasma (the accelerating plasma circulating step mentioned above) for returning the collected plasma to the centrifugal separator 20 via the first line 21 and the second line 22 is carried out. The accelerating plasma circulation is carried out at an initial flow rate in the range of 60~90 ml/min, a finally reached flow rate (preset flow rate) in the range of 120~180 ml/min, and a circulation time in the range of 20~50 sec so as to increase the flow rate in the range of 2~10 ml/min per second. In concert with the increase of the circulating speed of plasma, the rotational frequency of the rotor 142 is increased from the rotational frequency of the rotor at the end of blood collection to the rotational frequency during the collection of platelets. When the prescribed duration elapses, the accelerating plasma circulation is completed by terminating the increase of the rotational frequency of the rotor and subsequently terminating the circulation of plasma.

When the accelerating plasma circulation is completed, the second blood collection (the step for collecting plasma in a small amount) is carried out. The second blood collection consists in adding the anticoagulant under prescribed conditions and again collecting the whole blood meanwhile in a minute amount. The second blood collection is performed until the BC boundary which is the boundary between the plasma layer 131 and the buffy coat layer 132 is detected and is stopped when the BC boundary is detected.

After the second blood collection has been performed, the collection of platelets (the platelet collecting step mentioned above) and the collection of buffy coat (the buffy coat collecting step mentioned above) are carried out. The plasma is passed through the first line 21 and the second line 22 and entered into the centrifugal separator 20 at the flow rate of plasma during the collection of platelets (in the range of 200~450 ml/min). The platelets which have emanated from the centrifugal separator 20 are collected in the platelet collecting bag 26 and subsequently the buffy coat which has emanated from the centrifugal separator 20 is collected in the buffy coat collecting bag 27.

The operation of collecting platelets will be described in detail below with reference to the flow charts shown in FIG. 10~FIG. 15.

Figure 10B:
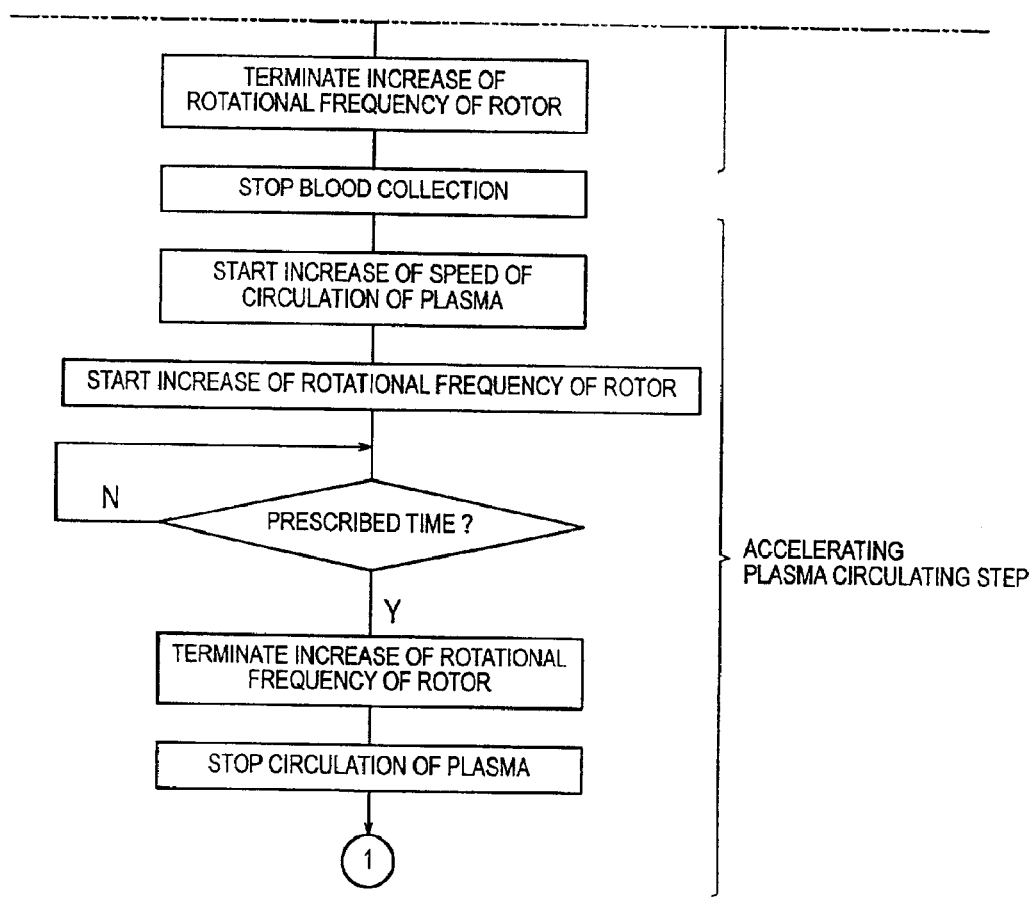
FIG. 10~FIG. 15 are flow charts intended to aid in the description of the operation of the platelet collecting apparatus of this invention.

The blood from the donor is analyzed in advance to determine the hematocrit value (HCT) and the determined hematocrit value is injected through the input device 61 of the controller roller 13 as illustrated in FIG. 10. The controller 13 computes the rotational frequency of the rotor of the centrifugal separator 20 at the end of the initial round of blood collection (the rotational frequency during blood collection) in accordance with the formula (1) using the introduced hematocrit value. The controller 13 also computes the time required for the arrival contemplated and the ratio of increase of the rotational frequency of the rotor.

Figure 9:
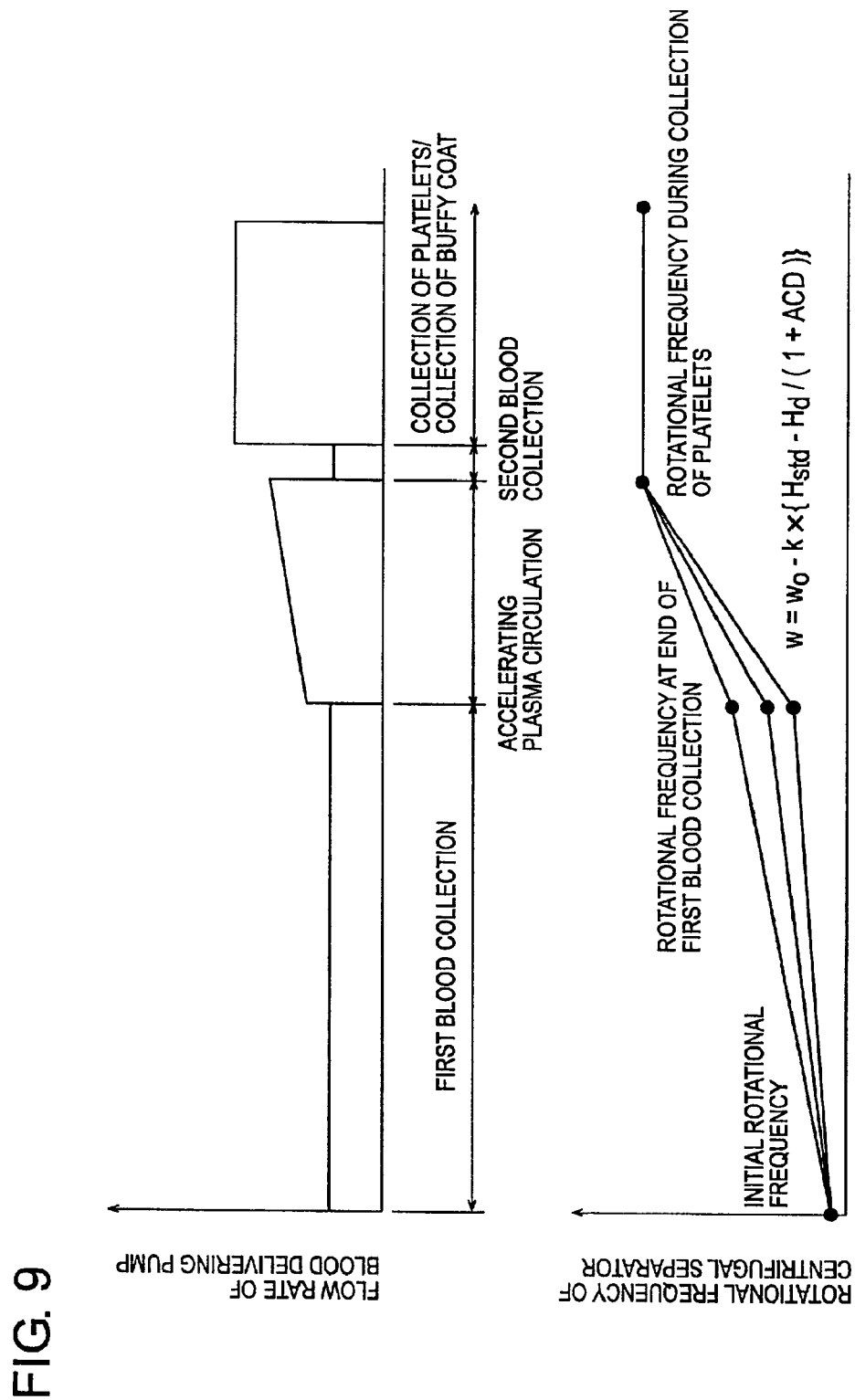
FIG. 9 is an explanatory diagram illustrating schematically the operation of the platelet collecting apparatus of this invention.

The third line 23 and the blood collection needle 29 are primed with the anticoagulant and the piercing needle of the blood collection needle is plunged into the donor to start the plasma collecting step (the first round of blood collection in FIG. 9).

The plasma collecting step actuates the blood delivering pump 11 and the liquid delivering pump 12 to collects the blood to which the anticoagulant has been added and actuates the centrifugal separator driving unit 10 to collect the plasma of a prescribed amount in the plasma collecting bag 25. The rotor 142 of the centrifugal separator 20 is rotated at the initial rotational frequency and the blood delivering pump 11 is actuated at the prescribed flow rate (60 ml/min, for example) to start the first blood collection. At the same time, the liquid delivering pump 12 which is an anticoagulant pump is also actuated at the prescribed flow rate (1/10 of the flow rate of the blood delivering pump 11, for example) to supply the anticoagulant (the ACD-A liquid, for example). The blood which has been collected from the donor is mixed with the anticoagulant, allowed to flow through the first line 21, passed through the chamber 21d, the first flow path switching means 81, and entered into the centrifugal separator 20. At this time, the sixth, fifth, second, and third flow path switching means 86, 85, 82, and 83 are in a closed state and the first and fourth flow path switching means 81, 84 are in an opened state. When the ACD-added blood is supplied to the centrifugal separator 20, the sterilized air which has entered the centrifugal separator 20 flows through the second line 22, passes through the fourth flow path switching means 84, and flows into the interior of the platelet collecting bag 26. When the collection of blood is started, the controller 13 begins to compute the amount of blood to be entered into the centrifugal separator 20. The rotational frequency of the rotor 142 is increased from the initial rotational frequency to the rotational frequency of the rotor during the course of blood collection in accordance with the computed ratio of increase of the rotational frequency of the rotor. Since the centrifugal separator 20 receives the supplied ACD-added blood while remaining in rotation, the blood is centrifuged in the centrifugal separator 20 and separated into the three layers, i.e. the plasma layer 131, the buffy coat (BC) layer 132, and the erythrocyte layer 133 as reckoned from the inner side outward. When the ACD-added blood of an amount (about 270 ml) exceeding the inner volume of the centrifugal separator 20 is supplied, the centrifugal separator 20 is completely filled with the blood and consequently forced to emit plasma through the outlet 144. The controller 13, on detecting the fact that the amount of blood delivered by the blood delivering pump 11 or the amount of blood injected into the centrifugal separator 20 has reached the prescribed level, in other words, the fact that the volume of erythrocytes in the centrifugal separator 20 has reached the prescribed level, stops the collection of blood by terminating the increase of the rotational frequency of the rotor and stopping the blood delivering pump 11. The controller 13 closes the fourth flow path switching means 84 and opens the third flow path switching means 83 to collect plasma in the plasma collecting bag 25. The process shifts to the accelerating plasma circulating step.

The accelerating plasma circulating step temporarily interrupts the collection of blood and actuates the centrifugal separator driving unit 10 to circulate the plasma in the plasma collecting bag 25 as accelerated to the centrifugal separator 20. At this time, the flow rate of the blood delivering pump 11 is started at a level in the range of 60~90 ml/min and accelerated until the final flow rate reaches a level in the range of 120~180 ml/min. The conditions for this acceleration are so set that the flow rate is increased by an increment in the range of 2~10 ml/min at intervals of one second. Further, the rotational frequency of the rotor during the course of the accelerating circulation is gradually increased from the rotational frequency at the end of the plasma collecting step or the end of the collection of blood toward the rotational frequency during the collection of platelets. The accelerating plasma circulating step is continued until the prescribed time (14~70 seconds, for example) has elapsed. When the prescribed time has elapsed, the increase of the rotational frequency of the rotor is terminated and the circulation of plasma by the blood delivering pump 11 is also terminated. After this circulating step is completed, the process shifts to the point (1) in the flow chart of FIG. 11 and performs the step for collecting the plasma in a small amount for use in the adjustment of boundary. The rotor 142 is continuing the rotation at the rotational frequency existing when the increase of the rotational frequency of the rotor is terminated.

Figure 11A:
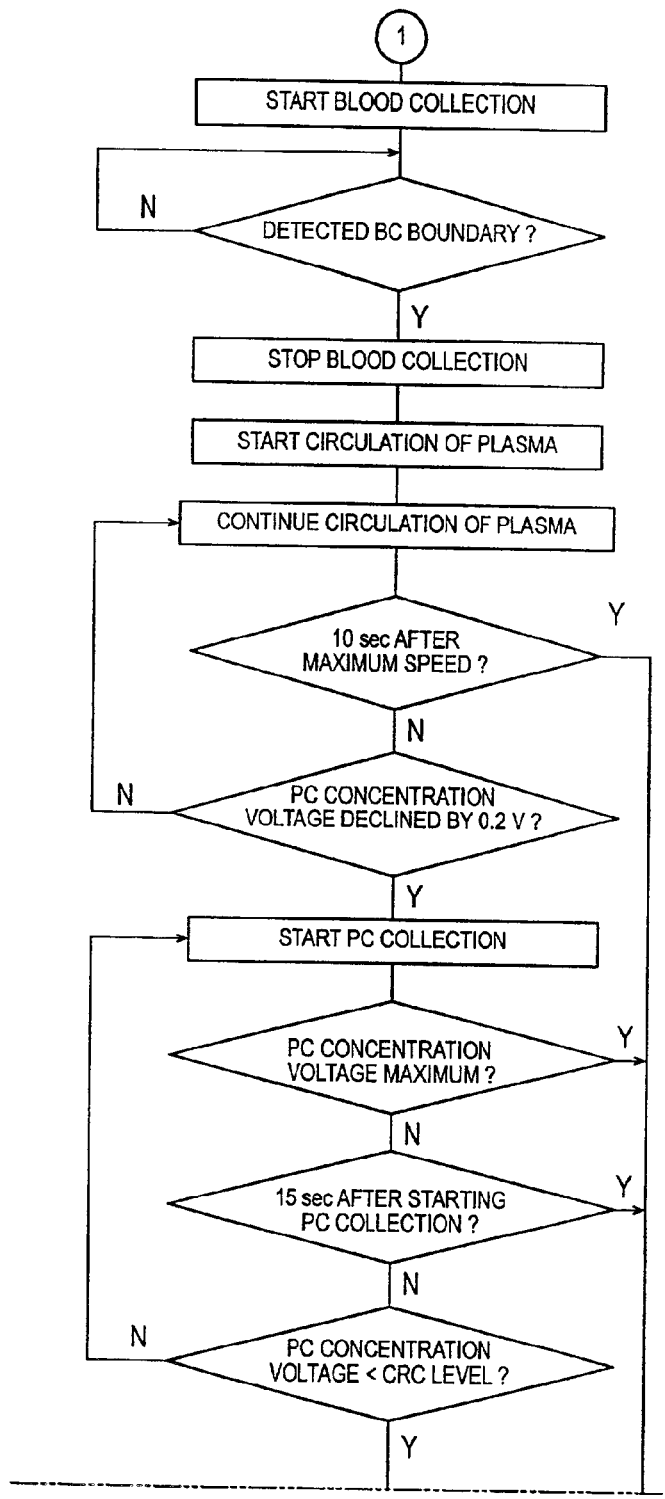
Figure 11B:
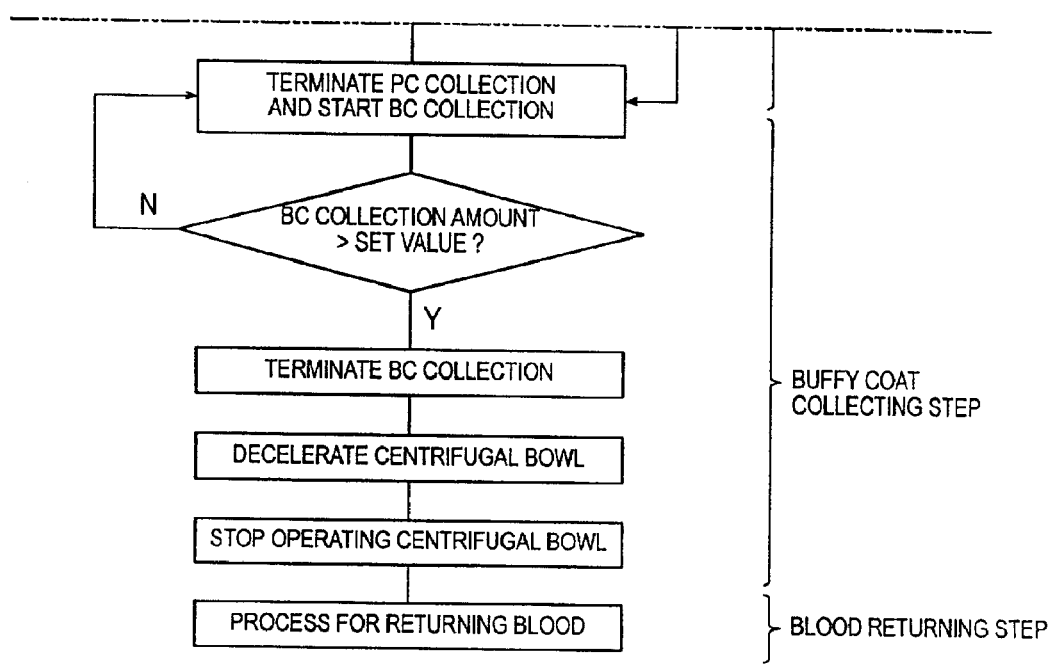

The step for collecting the plasma in a small amount, as illustrated in FIG. 11, fixes the position of the buffy coat layer during the process for collecting platelets subsequently without reference to the donor and, therefore, collects blood in an amount enough to permit supply of erythrocytes in a prescribed amount. Also in this collection of blood, the blood delivering pump 11 starts collecting blood at a prescribed flow rate (60 ml/min, for example). At this time, the liquid delivering pump 12 which is an anticoagulant pump supplies the anticoagulant (ACD-A liquid, for example) simultaneously at a prescribed flow rate (1/10 of the flow rate of the blood delivering pump 11, for example). The blood which has been collected from the donor is mixed with the anticoagulant, allowed to flow into the centrifugal separator 20 in rotation to effect the collection of plasma in a small amount. The controller 13 terminates the collection of blood at the time that the optical sensor 15 detects the BC boundary. When the step for collecting plasma in a small amount is completed, the controller 13 closes the first flow path switching means 81 and opens the second flow path switching means 82. The process shifts to the step for collecting platelets.

At the step for collecting platelets, the blood delivering pump 11 causes the plasma in the centrifugal separator 20 to flow into the centrifugal separator 20 at the flow rate of plasma during the collection of platelets (200~450 ml/min), expels the platelets from the interior of the centrifugal separator 20, and collects the platelets in the platelet collecting bag 26. At the platelet collecting step, the flow rate of the blood delivering pump 11 is maintained at a fixed level.

When the platelet collecting step is started, the turbidity sensor 14 detects the turbidity of the liquid passing therethrough. The turbidity is emitted as the magnitude of voltage from the sensor 14 and the signal consequently emitted is entered into the controller 13. When the platelets contained in the buffy coat layer which has been remaining in the centrifugal separator 20 flow out, the turbidity of the liquid passing the part of the turbidity sensor 14 becomes greater. At the time that the magnitude of output voltage from the turbidity sensor 14 has fallen to 0.2 V, the third flow path switching means 83 is closed, the fourth flow path switching means 84 is opened, and the platelet-rich plasma emanating from the centrifugal separator 20 is collected in the platelet collecting bag 26. The magnitude of output voltage issued from the turbidity sensor 14 is converted by the controller 13 into the concentration of platelets and the concentration of platelets in the platelet collecting bag 26 during the collection of platelets is computed. The concentration of platelets in the platelet collecting bag 26 reaches the maximum level temporarily and then declines. The platelet collecting step is terminated and shifted to the blood returning step at the time that the arrival of the concentration at the maximum level is detected.

In the platelet collecting apparatus 1 of the present embodiment, during every, except the last, round of the operation for collecting platelets, the buffy coat collecting step is executed prior to the execution of the blood returning step for returning the blood in the centrifugal separator 20 to the donor. Further, the buffy coat returning step for returning the collected buffy coat to the interior of the centrifugal separator 20 is executed prior to the execution of the subsequent plasma collecting step.

At the buffy coat collecting step, the buffy coat is emanated from the interior of the centrifugal separator 20 and collected in the buffy coat collecting bag 27. When the amount of the buffy coat so collected exceeds the prescribed level, the collection of buffy coat is terminated and the centrifugal separator 20 is decelerated and eventually stopped.

At the blood returning step, the controller 13 reverses the rotation of the blood delivering pump 11 and opens the first flow path switching means 81. The erythrocyte layer remaining in the centrifugal separator 20 is passed through the first line 21 and returned to the donor.

Consequently, the first round of the operation of collecting platelets is completed.

Figure 12A:
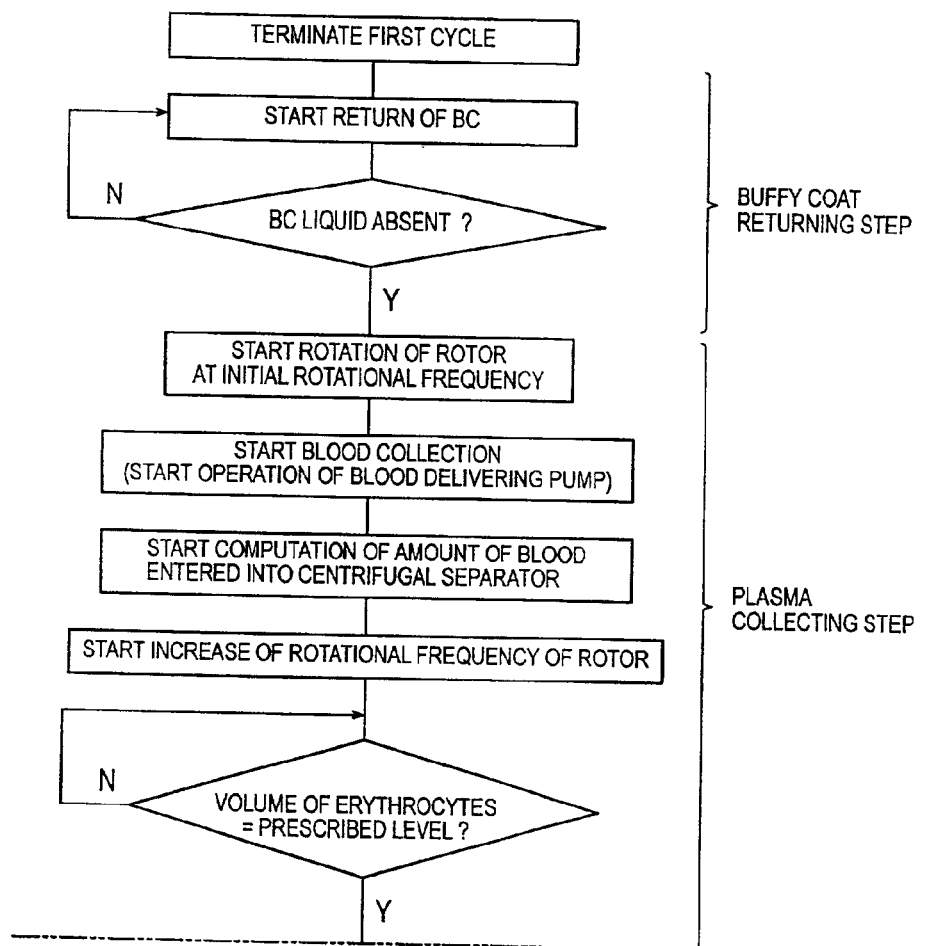
Figure 12B:
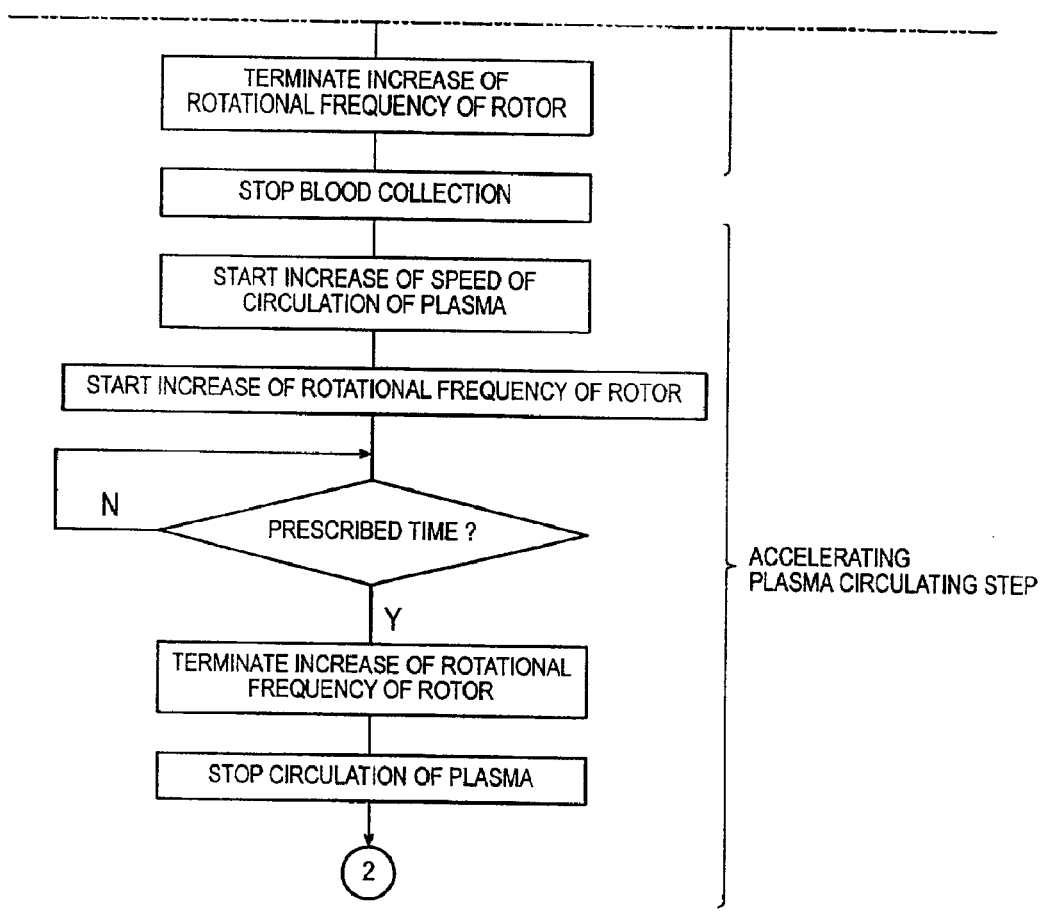

Subsequently, the process shifts to the second round of the operation of collecting platelets. The buffy coat returning step for returning the buffy coat collected by the first round of the platelet collecting step to the interior of the centrifugal separator 20 is executed prior to the subsequent plasma collecting step as illustrated in FIG. 12. When the process shifts to the buffy coat returning step, the controller 13 rotates the rotor 142 of the centrifugal separator 20 at the calculated or present rotational frequency and opens the fifth and fourth flow path switching means 85, 84 and actuates the blood delivering pump 11 at the prescribed flow rate (100 ml/min for default). The buffy coat contained in the buffy coat collecting bag 27 is passed through the fifth flow path switching means 85 and supplied to the centrifugal separator 20. The air in the centrifugal separator 20 is passed through the second line 22 and the fourth flow path switching means 84 and delivered to the platelet collecting gas 26. The buffy coat returning step is terminated after the blood delivering pump 11 has rotated in an amount conforming to the amount of buffy coat collected.

Figures 13, 13A:
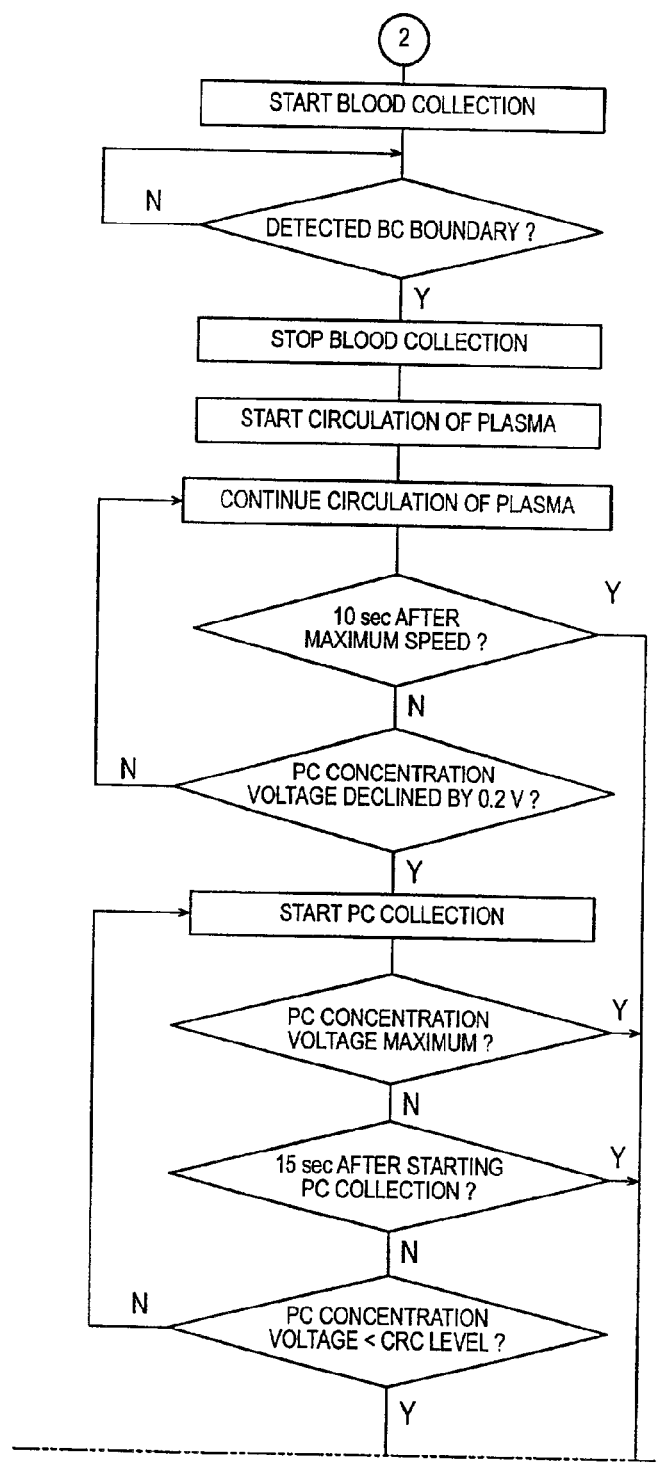
Figure 13B:
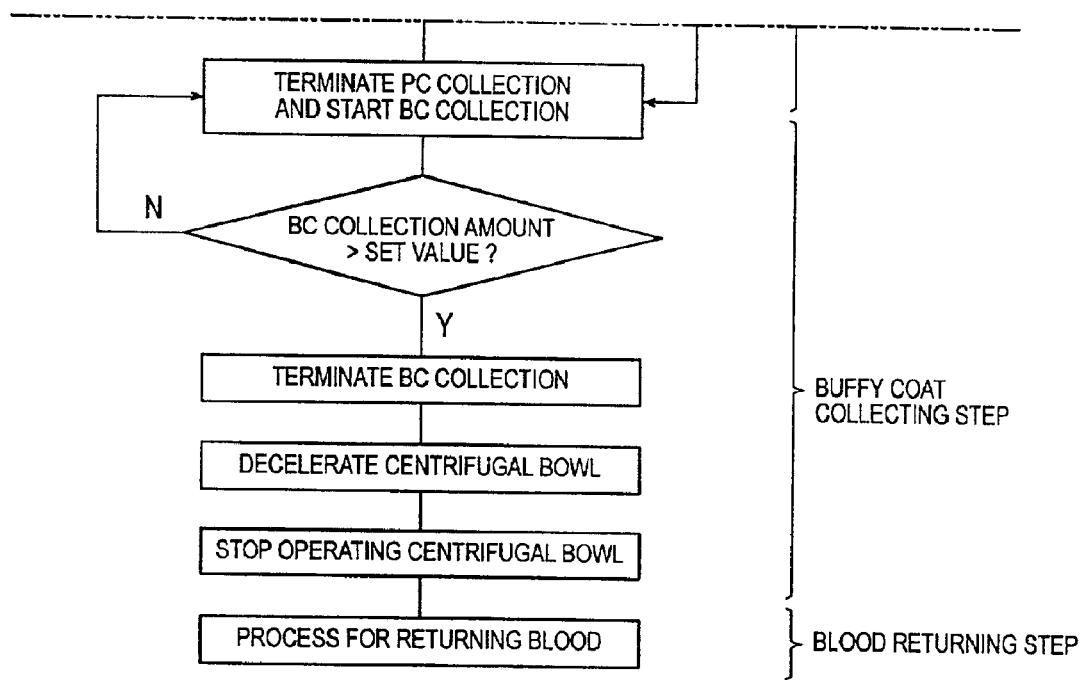

Then, in the same manner as described above, the plasma collecting step and the accelerating plasma circulating step are executed and, after the shift of the process to the point (2) in the flow chart of FIG. 13, the step for collecting plasma in a small amount, the platelet collecting step, the buffy coat collecting step, and the blood returning step are executed sequentially in the order mentioned. Consequently, the second round of the operation of collecting platelets is completed. The operation of collecting platelets which is performed as described above up to the present number of repetitions. The buffy coat collecting step is not executed when the second round forms constitutes itself the last round of the operation of collecting platelets.

Figures 14, 14A:
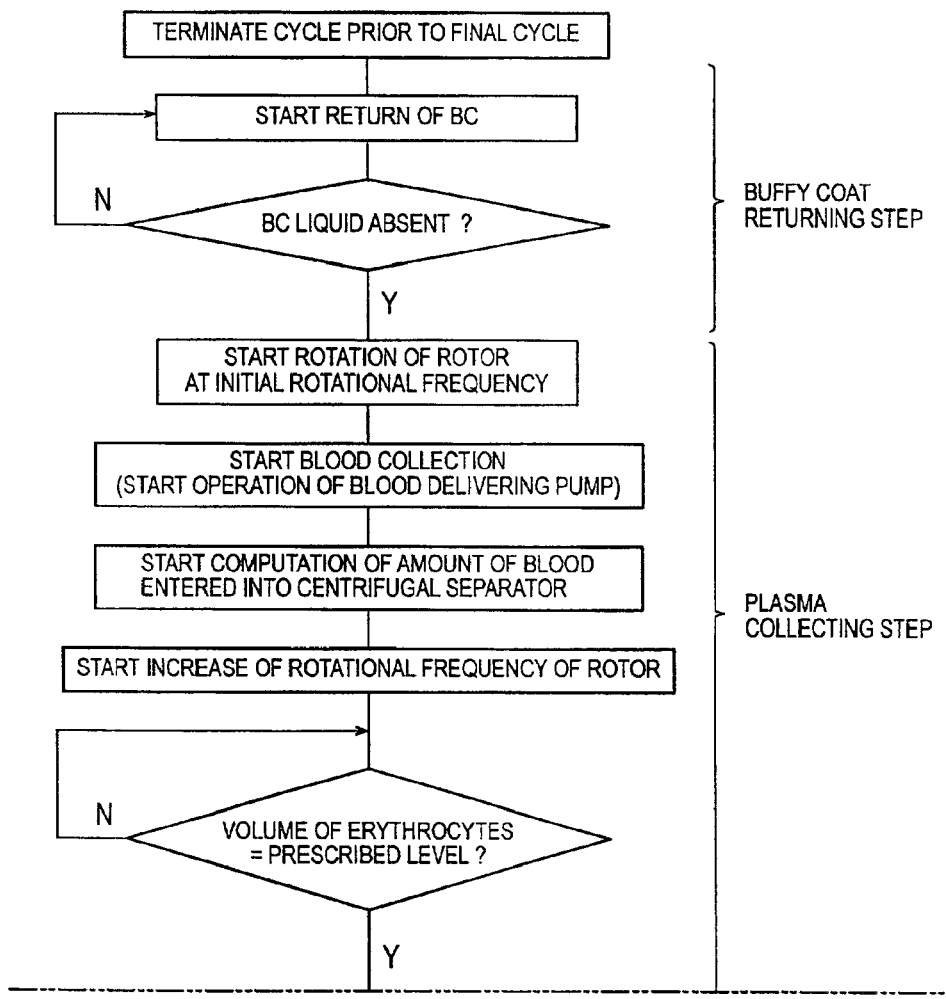
Figure 14B:
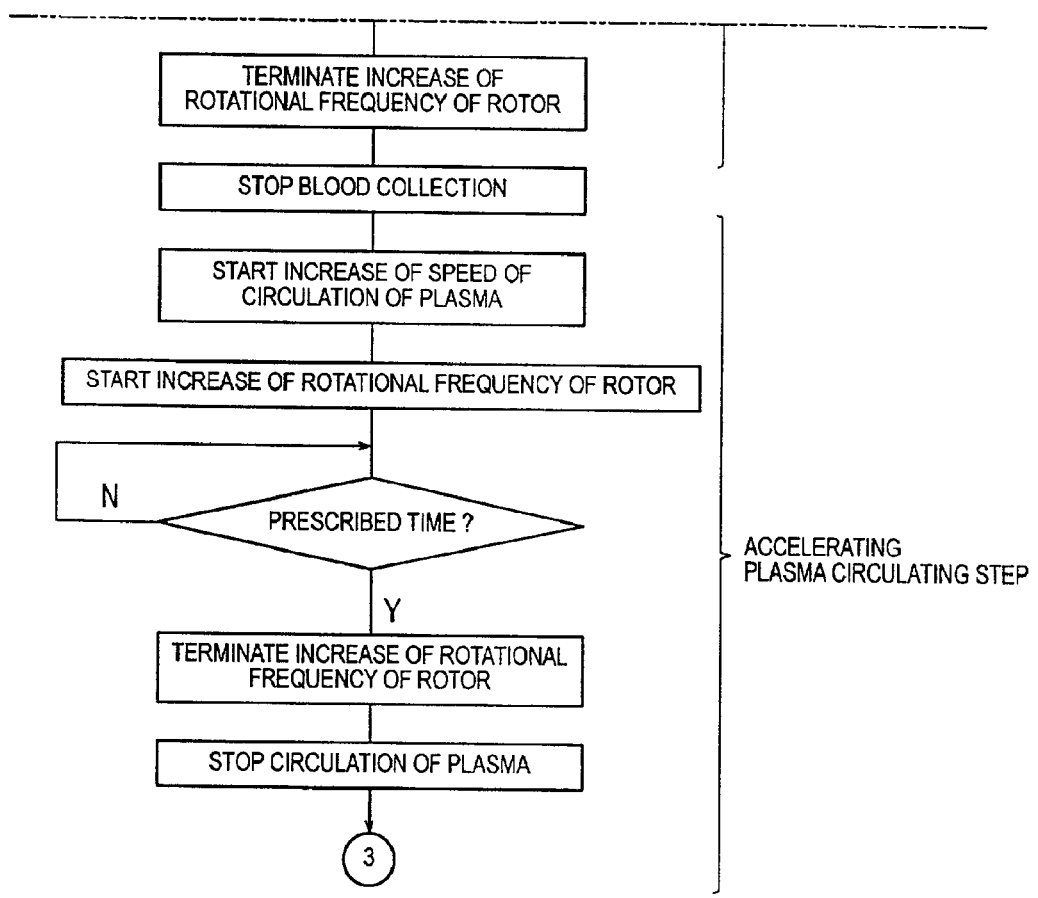
Figure 15B:
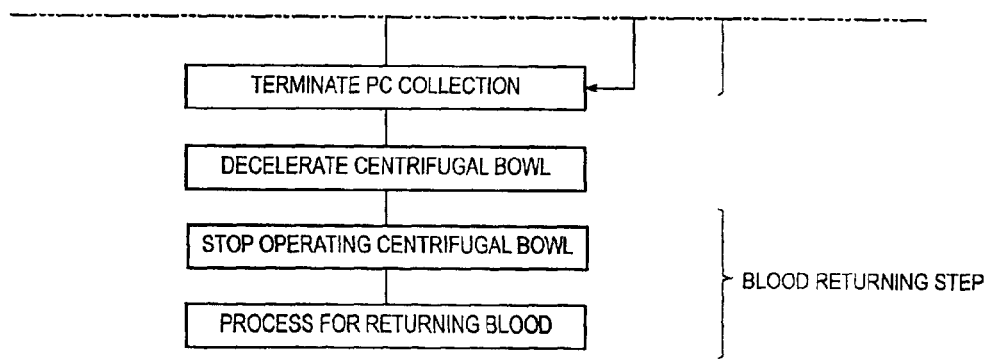

Subsequently, the process shifts to the final round of the operation for collecting platelets illustrated in FIG. 14. In this embodiment, the third round is contemplated as the last round. The last round of the operation for collecting platelets may occur on or after the fourth round. In this case, the process of the second round of the operation for collecting platelets is executed in all, except the last, rounds.

In the same manner as described above, the buffy coat returning step, the plasma collecting step, and the accelerating plasma circulating step are executed as illustrated in FIG. 4. After the process has shifted to the point (3) in the flow chart of FIG. 15, the step for collecting plasma in a small amount, the platelet collecting step, and the blood returning step are executed sequentially in the order mentioned. Consequently, all the operations for collection of platelets is completed.

EXAMPLE

A platelet collecting apparatus constructed as illustrated in FIG. 3 and FIG. 4 was prepared.

The whole blood from a donor, while having an anticoagulant added thereto at a stated ratio (1/10 based on the amount of the whole blood), was collected at a stated flow rate of 60 ml/min via the first line 21 into the centrifugal separator 20 kept in rotation at a stated rotational frequency which will be described specifically hereinafter. The collection was continued until the volume of blood cells in the centrifugal separator 20 reached 135 ml, a stated level. The rotational frequency of the centrifugal separator 20 was gradually increased in concert with the increase in the amount of blood cells in the centrifugal separator 20, from the initial rotational frequency 3,750 rpm until the prescribed rotational frequency at the end of the first round of blood collection was reached. The rotational frequency at the end of the first round of blood collection was computed in accordance with the following formula (6) and in conformity with the hematocrit value of the donor. This formula (6) set the rotational frequency at the end of the first round of blood connection at a level lower than 4,750 rpm when the hematocrit value of the donor was smaller than the standard hematocrit value 40% and at a level higher when the hematocrit value of the donor was larger. The platelet collecting apparatus used herein was furnished with a hematocrit value input part and a function of computing the rotational frequency at the end of the first round of blood collection using the following formula (6).

$$w = 4{,}750 - 10 \times (40 - Hd) \quad (6)$$

wherein w=the rotational frequency (rpm) at the end of the first round of blood collection Hd=the hematocrit value (%) of the donor The plasma which overflowed the centrifugal separator 20 during the process of the first collection of blood was collected in the plasma collecting bag 25 until the volume of erythrocytes in the centrifugal separator 20 reached a prescribed level.

The first flow path switching means 81 was closed to terminate the first process of blood collection at the time that the volume of erythrocytes in the centrifugal separator 20 reached the prescribed level of 135 ml. Subsequently, the second flow path switching means 82 was opened to perform accelerating circulation of the plasma collected in the plasma collecting bag 25 for 30 seconds, a period required for the initial rate of circulation, 80 ml/min, to reach the final rate of circulation, 140 ml/min and, at the same time, to increase the rotational frequency of the centrifugal separator 20 to the rotational frequency, 5,400 rpm, during the collection of platelets. After the step for accelerating circulation/accelerating centrifugation had been completed, the second flow path switching means 82 was closed and the first flow path switching means 81 was opened to perform the collection of blood again via the first line 21 into the centrifugal separator 20 rotating at the rotational frequency during the platelet collection described above until the optical sensor 15 detected the boundary of blood cells (BC boundary).

In the process for collecting platelets, the first flow path switching means 81 was closed to terminate the second step for blood collection and the second flow path switching means 82 was opened to allow the plasma collected in the plasma collecting bag 25 to flow at the flow rate of plasma, 250 ml/min, during the collection of platelets into the centrifugal separator rotating at 5,400 rpm. When the turbidity sensor 14 detected the emanation of platelets, the third flow path switching means 83 was closed and the fourth flow path switching means 84 was opened to collect the platelet-rich plasma flowing out of the centrifugal separator 20 in the platelet collecting bag 26.

When the turbidity sensor 14 detected the absence of discernible emanation of platelets, the entry of plasma into the centrifugal separator 20 was stopped and the fourth flow path switching means 84 was closed and the fifth flow path switching means 85 was opened to collect the buffy coat emanating from the centrifugal separator 20 into the buffy coat collecting bag 27. Thereafter, the rotation of the centrifugal separator 20 was stopped and all the flow path switching means 81~86 were closed.

In the process for returning the blood, the rotation of the blood delivering pump 11 was reversed and the first flow path switching means 81 was opened to return the blood cells remaining in the centrifugal separator 20 to the donor via the first line 21.

Table 1 shows the hematocrit values of donors, the efficiencies of collection of platelets from the donors for the manufacture of platelet preparations, and the numbers of leucocytes suffered to be contaminated as reduced to 10 units dose.

TABLE 1

| Hematocrit value of donor (%) | Efficiency of collection of platelets (%) | Contamination of leucocytes ($10^6$ cells/10 units dose) |
|---|---|---|
| 42.1 | 81.4 | 12.3 |
| 45.5 | 79.8 | 34.4 |
| 39.2 | 82.4 | 7.3 |
| 37.8 | 84.2 | 3.8 |

COMPARATIVE EXAMPLE 1

A platelet collecting apparatus constructed as illustrated in FIG. 3 and FIG. 4 was prepared.

The whole blood from a donor, while having an anticoagulant added thereto at a stated ratio (1/10 based on the amount of the whole blood), was collected at a stated flow rate of 60 ml/min via the first line 21 into the centrifugal separator 20 kept in rotation at 4,750 rpm until the volume of blood cells in the centrifugal separator 20 reached a stated level of 135 ml. The rotational frequency of the centrifugal separator 20 was fixed at 4,750 rpm and was not varied in accordance with the hematocrit value of the donor.

The plasma which overflowed the centrifugal separator 20 during the process of the first collection of blood was collected in the plasma collecting bag 25 until the volume of erythrocytes in the centrifugal separator 20 reached a prescribed level.

At the time that the volume occupied by erythrocytes in the centrifugal separator 20 reached the prescribed level of 135 ml, the first flow path switching means 81 was closed to terminate the first process for blood collection. Subsequently, the second flow path switching means 82 was opened to perform accelerating circulation of the plasma collected in the plasma collecting bag 25 for 30 seconds, a period required for the initial rate of circulation, 80 ml/min, to reach the final rate of circulation, 140 ml/min. Again at this time, the rotational frequency of the centrifugal separator 20 was fixed at 4,750 rpm. After the step for accelerating circulation had been completed, the second flow path switching means 82 was closed and the first flow path switching means 81 was opened to perform the collection of blood again via the first line 21 into the centrifugal separator 20 rotating at a rotational frequency of 4,750 rpm until the optical sensor 15 detected the boundary of blood cells.

In the process for collecting platelets, the first flow path switching means 81 was closed to terminate the second process for blood collection and the second flow path switching means 82 was opened to allow the plasma collected in the plasma collecting bag 25 to flow at a flow rate of plasma, 200 ml/min, existing during the collection of platelets into the centrifugal separator 20 kept rotating at 4,750 rpm. When the turbidity sensor 14 detected the emanation of platelets, the third flow path switching means 83 was closed and the fourth flow path switching means 84 was opened to collect the platelet-rich plasma emanating from the centrifugal separator 20 in the platelet collecting bag 26.

When the turbidity sensor 14 detected the absence of discernible emanation of platelets, the entry of plasma into the centrifugal separator 20 was stopped and the fourth flow path switching means 84 was closed and the fifth flow path switching means 85 was opened to collect the buffy coat emanating from the centrifugal separator 20 into the buffy coat collecting bag 27. Thereafter, the rotation of the centrifugal separator 20 was stopped and all the flow path switching means 81~86 were closed.

In the process for returning the blood, the rotation of the blood delivering pump 11 was reversed and the first flow path switching means 81 was opened to return the blood cells remaining in the centrifugal separator 20 to the donor through the first line 21.

Table 2 shows the hematocrit values of donors, the efficiencies of collection of platelets from the donors for the manufacture of platelet preparations, and the numbers of leucocytes suffered to be contaminated as reduced to 10 units dose.

TABLE 2

| Hematocrit value of donor (%) | Efficiency of collection of platelets (%) | Contamination of leucocytes ($10^6$ cells/10 units dose) |
| --- | --- | --- |
| 40.5 | 80.3 | 89.3 |
| 38.4 | 58.3 | 132.9 |
| 46.1 | 44.2 | 323.1 |
| 35.9 | 52.8 | 34.1 |

Comparison between Table 1 and Table 2 reveals that the platelet preparation obtained in Example suffered less dispersion between products and less contamination of leukocytes than that obtained in Comparative Example. The better results are ascribable to the effect of increasing the rotational frequency of the centrifugal separator 20 in conformity with the amount of blood cells and the hematocrit value obtained during the course of blood collection and the effect of increasing simultaneously the resistance generated by the motion of the plasma and the centrifugal force during the motion of plasma in the interstices between the adjacent blood cells.

This invention does not need to be limited solely to the preferred embodiment described above but may be variously altered or modified without departure from the technical concept of this invention This application is based on Patent Application No. 2000-360786 filed on Nov. 28, 2000 in Japan, the content of which is hereby incorporated by reference.

What is claimed is:

1. A platelet collecting apparatus comprising:
    a centrifugal separator possessing a rotatable rotor having a blood storing space formed therein and an inlet and an outlet both communicating with said blood storing space and centrifugally separating the blood introduced through said inlet inside said blood storing space by virtue of the rotation of said rotor;
    a first line for allowing the flow of the blood entering said centrifugal separator;
    a second line for allowing the flow of the blood emanating from said centrifugal separator;
    a plasma collecting bag connected to said first line and said second line so as to collect the plasma emanating from said centrifugal separator and return the collected plasma to said centrifugal separator;
    a platelet collecting bag connected to said second line so as to collect the platelets emanating from said centrifugal separator;
    a blood delivering pump disposed in said first line; and
    a controller for controlling the operation of said rotor of said centrifugal separator and the operation of said blood delivering pump,
    wherein said controller is programmed to increase the rotational frequency of said rotor in conformity with the increase of the volume of erythrocytes in said centrifugal separator during blood collection.

2. A platelet collecting apparatus according to claim 1, wherein said controller is further furnished with
    a function of increasing the flow rate of circulation by said blood delivering pump to cause the plasma collected in said plasma collecting bag to be circulated with acceleration between said plasma collecting bag and said centrifugal separator; and
    a function of varying the rotational frequency of said rotor in conformity with the speed of the circulation of said plasma caused by said function of accelerating circulation.

3. A platelet collecting apparatus according to claim 2, wherein said controller, while the plasma is circulated as accelerated by said function of accelerating circulation, increases the rotational frequency of said rotor in conformity with the increase of the flow rate of circulation produced by said blood delivering pump.

4. A platelet collecting apparatus according to claim 1, wherein said controller during the course of blood collection sequentially increases the rotational frequency of said rotor to a predetermined rotational frequency in conformity with the amount of the blood entered into said centrifugal separator.

5. A platelet collecting apparatus according to claim 1, which is further furnished with an input device for effecting entry of a hematocrit value and wherein said controller is furnished with a function of computing the rotational frequency of the rotor of said centrifugal separator at the end of a first round of blood collection based on the input of the hematocrit value and said controller, during the course of blood collection, sequentially increases the rotational frequency of said rotor to the computed rotational frequency of said rotor in conformity with the amount of the blood entered into said centrifugal separator.

6. A platelet collecting apparatus according to claim 1, which is further furnished with a measuring device for measuring a hematocrit value and wherein said controller is furnished with a function of computing the rotational frequency of the rotor of said centrifugal separator at the end of a first round of blood collection based on the determined hematocrit value and said controller, during the course of blood collection, sequentially increases the rotational frequency of said rotor to the computed rotational frequency of said rotor in conformity with the amount of the blood entered into said centrifugal separator.

7. A platelet collecting apparatus according to claim 1, which is further furnished with a memory device for memorizing the amount of blood delivered per unit amount of operation of said blood delivering pump and a detecting device for detecting the amount of operation of said blood delivering pump and wherein said controller computes the amount of blood entered in said centrifugal separator based on the memorized amount of blood delivered per unit amount of operation and the detected amount of operation.

8. A platelet collecting apparatus according to claim 7, wherein said blood delivering pump is formed of a roller pump and said detecting device is formed of a means for detecting the amount of rotation of said roller pump.

9. A platelet collecting apparatus comprising:
   a centrifugal separator possessing a rotatable rotor having a blood storing space formed therein and an inlet and an outlet both communicating with said blood storing space and centrifugally separating the blood introduced through said inlet inside said blood storing space by virtue of the rotation of said rotor;
   a first line for allowing the flow of the blood entering said centrifugal separator;
   a second line for allowing the flow of the blood emanating from said centrifugal separator;
   a plasma collecting bag connected to said first line and said second line so as to collect the plasma emanating from said centrifugal separator and return the collected plasma to said centrifugal separator;
   a platelet collecting bag connected to said second line so as to collect the platelets emanating from said centrifugal separator;
   a blood delivering pump disposed in said first line; and
   a controller for controlling the operation of said rotor of said centrifugal separator and the operation of said blood delivering pump,
   wherein said controller is programmed to increase the flow rate of circulation by said blood delivering pump to cause the plasma collected in said plasma collecting bag to be circulated with acceleration between said plasma collecting bag and said centrifugal separator; and
   to increase the rotational frequency of said rotor in conformity with the increase in the flow rate of circulation produced by said blood delivering pump.

10. A method for collecting blood platelets by the use of a platelet collecting apparatus comprising;
    a centrifugal separator possessing a rotatable rotor having a blood storing space formed therein and an inlet and an outlet both communicating with said blood storing space and centrifugally separating the blood introduced through said inlet inside said blood storing space by virtue of the rotation of said rotor;
    a first line for allowing the flow of the blood entering said centrifugal separator;
    a second line for allowing the flow of the blood emanating from said centrifugal separator;
    a plasma collecting bag connected to said first line and said second line so as to collect the plasma emanating from said centrifugal separator and return the collected plasma to said centrifugal separator;
    a platelet collecting bag connected to said second line so as to collect the platelets emanating from said centrifugal separator;
    a blood delivering pump disposed in said first line; and
    a controller for controlling the operation of said rotor of said centrifugal separator and the operation of said blood delivering pump,
    wherein said method comprises blood collection in which the rotational frequency of said rotor sequentially increases to a predetermined rotational frequency in conformity with the amount of blood entered into said centrifugal separator via said first line during the course of blood collection.

11. A method for collecting platelet according to claim 10, wherein said blood collection involves increasing the rotational frequency of said rotor in conformity with the increase of the volume of erythrocytes in said centrifugal separator during the course of blood collection.

12. A method for collecting platelet according to claim 10, further comprising plasma circulation in which the plasma collected in said plasma collecting bag is circulated between said plasma collecting bag and said centrifugal separator subsequent to said blood collection.

13. A method for collecting platelet according to claim 12, wherein in said plasma circulation the flow rate of circulation by said blood delivering pump is increased to cause the plasma collected in said plasma collecting bag to be circulated with acceleration between said plasma collecting bag and said centrifugal separator.

14. A method for collecting platelet according to claim 12, wherein in said plasma circulation, while the plasma is circulated with acceleration, the rotational frequency of said rotor is increased in conformity with the increase of the flow rate of circulation produced by said blood delivering pump.

15. A method for collecting platelet according to claim 12, further comprising platelet collection in which the flow rate of circulation by said blood delivering pump is increased to cause the plasma collected in said plasma collecting bag to be fed with acceleration from said plasma collecting bag to said centrifugal separator subsequent to said plasma circulation.

* * * * *